(12) United States Patent
Beliveau et al.

(10) Patent No.: US 8,487,072 B2
(45) Date of Patent: Jul. 16, 2013

(54) COMPOUNDS FOR STIMULATING P-GLYCOPROTEIN FUNCTION AND USES THEREOF

(75) Inventors: Richard Beliveau, Montreal (CA); Michel Demeule, Beaconsfield (CA); Stephane Barakat, Montreal (CA); Jonathan Michaud-Levesque, Montreal (CA)

(73) Assignee: Angiochem Inc., Montreal (CA)

( * ) Notice: Subject to any disclaimer, the term of this patent is extended or adjusted under 35 U.S.C. 154(b) by 237 days.

(21) Appl. No.: 12/446,434

(22) PCT Filed: Oct. 19, 2007

(86) PCT No.: PCT/CA2007/001861
§ 371 (c)(1),
(2), (4) Date: May 27, 2011

(87) PCT Pub. No.: WO2008/046228
PCT Pub. Date: Apr. 24, 2008

(65) Prior Publication Data
US 2011/0218152 A1    Sep. 8, 2011

Related U.S. Application Data

(60) Provisional application No. 60/852,678, filed on Oct. 19, 2006.

(51) Int. Cl.
*A61K 38/10* (2006.01)
*C07K 7/08* (2006.01)

(52) U.S. Cl.
USPC .......................................... 530/300; 514/1.1

(58) Field of Classification Search
None
See application file for complete search history.

(56) References Cited

U.S. PATENT DOCUMENTS

| | | | |
|---|---|---|---|
| 7,557,182 B2 | 7/2009 | Beliveau et al. | |
| 7,902,156 B2 | 3/2011 | Beliveau et al. | |
| 2002/0086384 A1 | 7/2002 | Levine et al. | |
| 2006/0182684 A1 | 8/2006 | Beliveau | |
| 2009/0016959 A1 | 1/2009 | Beliveau et al. | |
| 2009/0082277 A1 | 3/2009 | Beliveau et al. | |
| 2010/0256055 A1 | 10/2010 | Castaigne et al. | |
| 2010/0297120 A1 | 11/2010 | Beliveau et al. | |

FOREIGN PATENT DOCUMENTS

| | | |
|---|---|---|
| CA | 2 421 041 A1 | 5/2002 |
| EP | 1 466 924 A1 | 10/2004 |
| GB | 2 360 453 A | 9/2001 |
| WO | WO 97/40160 | 10/1997 |
| WO | WO 99/46575 | 9/1999 |
| WO | WO 02/20768 A2 | 3/2002 |
| WO | WO 2004/060403 A2 | 7/2004 |
| WO | WO 2006/086870 A1 | 8/2006 |
| WO | WO 2007/009229 A1 | 1/2007 |
| WO | WO 2008/144919 A1 | 12/2008 |
| WO | WO 2009/079790 A1 | 7/2009 |
| WO | WO 2009/127072 A1 | 10/2009 |
| WO | WO 2010/043047 A1 | 4/2010 |
| WO | WO 2010/043049 A1 | 4/2010 |
| WO | WO 2010/063122 A1 | 6/2010 |
| WO | WO 2010/063123 A1 | 6/2010 |
| WO | WO 2010/063124 A1 | 6/2010 |
| WO | WO 2010/069074 A1 | 6/2010 |
| WO | WO 2010/121379 A1 | 10/2010 |
| WO | WO 2010/142035 A1 | 12/2010 |
| WO | WO 2011/000095 A1 | 1/2011 |
| WO | WO 2011/041897 A1 | 4/2011 |

OTHER PUBLICATIONS

Kesari et al. Phase II study of temozolomide, thalidomide, and celecoxib for newly diagnosed glioblastoma in adults, Jun. 2008, Neuro Oncology 10(3):300-308).*
Barakat et al., "Modulation of p-glycoprotein function by caveolin-1 phosphorylation," *J. Neurochem.* 101: 1-8 (2007).
Barakat et al., "Regulation of brain endothelial cells migration and angiogenesis by P-glycoprotein/caveolin-1 interaction," *Biochem. Biophys. Res. Commun.* 372: 440-446 (2008).
Demeule et al., "P-glycoprotein is localized in caveolae in resistant cells and in brain capillaries," *FEBS Lett.* 466: 219-224 (2000).
Demeule et al., "Drug transport to the brain: key roles for the efflux pump P-glycoprotein in the blood-brain barrier," *Vascul. Pharmacol.* 38: 339-348 (2002).
Jodoin et al., "P-glycoprotein in blood-brain barrier endothelial cells: interaction and oligomerization with caveolins," *J. Neurochem.* 87: 1010-1023 (2003).
Okamoto et al., "Caveolins, a family of scaffolding proteins for organizing "preassembled signaling complexes" at the plasma membrane," *J. Biol. Chem.* 273: 5419-5422 (1998).
International Search Report and Written Opinion for International Application No. PCT/CA2007/001861, dated Feb. 4, 2008 (16 pages).
EPO Communication enclosing the Extended European Search Report for European Application No. 07816012.4, dated Sep. 24, 2010 (14 pages).
Chu et al., "Detection of soluble P-glycoprotein in culture media and extracellular fluids," *Biochem. Biophys. Res. Commun.*, 1994, 203:506-512, (7 pages).
UniProtKB Entry P08183, MDR1_HUMAN, Multidrug resistance proteins 1 (EC 3.6.3.44) (ATP-binding cassette DE subfamily B member 1) (P-glycoprotein 1) (CD243 antigen), 2006, (6 pages).
EPO Communication for European Patent Application No. 07816012.4, dated Oct. 10, 2012, (9 pages).

* cited by examiner

*Primary Examiner* — John Ulm
(74) *Attorney, Agent, or Firm* — Clark & Elbing LLP; Kristina Bieker-Brady

(57) ABSTRACT

The present invention is directed to polypeptides (e.g., fragments) derived from P-glycoprotein and caveolin-1 which are capable of inhibiting the interaction between these two proteins. Inhibition of this interaction leads to increase of efflux of compounds that are transported by P-gp. The invention further includes methods of treating patients having diseases that benefit from increased P-gp-mediated efflux. Such diseases include neoplasms such as cancer and neurological diseases such as neurodegenerative diseases.

4 Claims, 6 Drawing Sheets

Ctrl   bFGF   pepCav   pepPgp

FIG. 5

```
Human P-glycoprotein 1 mdlegdrngg akkknffkln nksekdkkek kptvsvfsmf rysnwldkly mvvgtlaaii
  61 hgaglplmml vfgemtdifa nagnledlms nitnrsdind tqffmnleed mtryayyysg
 121 igagvlvaay iqvsfwclaa grqihkirkq ffhaimrqei gwfdvhdvge lnrltddvs
 181 kinegigdki gmffqsmatf ftgfivgftr gwkltlvila ispvlglsaa vwakilssft
 241 dkellayaka gavaeevlaa irtviafggq kkelerynkn leeakrigik kaitanisig
 301 aaflliyasy alafwygttl vlsgeysigq vltvffsvli gafsvgqasp sieafanarg
 361 aayeifkiid nkpsidsysk sghkpdnikg nlefrnvhfs ypsrkevkil kglnlkvqsg
 421 qtvalvgnsg cgksttvqlm qrlydptegm vsvdgqdirt invrflreii gvvsqepvlf
 481 attiaeniry grenvtmdei ekavkeanay dfimklphkf dtlvgergaq lsggqkqria
 541 iaralvrnpk illldeatsa ldteseavvq valdkarkgr ttiviahrls tvrnadviag
 601 fddgvivekg nhdelmkekg iyfklvtmqt agnevelena adeskseida lemssndsrs
 661 slirkrstrr svrgsqaqdr klstkealde sippvsfwri mklnltewpy fvvgvfcaii
 721 ngglqpafai ifskiigvft riddpetkrq nsnlfsllfl algiisfitf flqgftfgka
 781 geiltkrlry mvfrsmlrqd vswfddpknt tgalttrlan daaqvkgaig srlavitqni
 841 anlgtgiiis fiygwqltll llaivpiiai agvvemkmls gqalkdkkel egsgkiatea
 901 ienfrtvvsl tqeqkfehmy aqslqvpyrn slrkahifgi tfsftqammy fsyagcfrfg
 961 aylvahklms fedvllvfsa vvfgamavgq vssfapdyak akisaahiim iiektplids
1021 ysteglmpnt legnvtfgev vfnyptrpdi pvlqglslev kkgqtlalvg ssgcgkstvv
1081 qllerfydpl agkvlldgke lkrlnvqwlr ahlgivsqep ilfdcsiaen iaygdnsrvv
1141 sqeeivraak eanihafies lpnkystkvg dkgtqlsggq kqriaiaral vrqphillld
1201 eatsaldtes ekvvqealdk aregrtcivi ahrlstiqna dlivvfqngr vkehgthqql
1261 laqkgiyfsm vsvqagtkrq Human Caveolin-1

1 msggkyvdse ghlytvpire qgniykpnnk amadelsekq vydahtkeid lvnrdpkhln
  61 ddvvkidfed viaepegths fdgiwkasft tftvtkywfy rllsalfgip maliwgiyfa
 121 ilsflhiwav vpciksflie iqcisrvysi yvhtvcdplf eavgkifsnv rinlqkei
```

COMPOUNDS FOR STIMULATING P-GLYCOPROTEIN FUNCTION AND USES THEREOF

CROSS-REFERENCE TO RELATED APPLICATIONS

This application is the National Stage of International Application No. PCT/CA2007/001861, filed Oct. 19, 2007, which claims benefit of U.S. Application No. 60/852,678, filed Oct. 19, 2006.

BACKGROUND OF THE INVENTION

The invention relates to the field of therapeutic compounds, their uses, methods of use and compositions comprising them. This invention also relates to the treatment of diseases resulting from accumulation of P-glycoprotein substrates. This invention also relates to the treatment of diseases associated with cellular migration and/or angiogenesis and neurological diseases.

ABC (ATP-Binding Cassette) transporters superfamily members are expressed on most mammalian tissues with excretory and/or barrier function. These transporters are involved in unidirectional substrate translocation and use ATP as the energy source to activate the extrusion process. ABC transporters appear to have developed as a mechanism to protect the body from harmful substances.

P-glycoprotein (P-gp) is an ABC transporter, product of the MDR1 gene, found in the liver, gut, gonads, kidneys, biliary system, brain, and other organs. P-glycoprotein is an efflux pump protecting the structural and functional integrity of the organs and tissues on which it is expressed. P-glycoprotein is localized at the plasma membrane, more specifically in microdomains enriched in cholesterol called caveolae. Caveolae may act as signaling platforms and can be identified by the presence of specific markers such as caveolin-1, -2, and -3. This particular localization seems to be important for P-gp ATPase and transport activities. Recent work suggests that two P-gp populations co-exist in the plasma membrane surrounded by different cholesterol concentration in the P-gp closed microenvironment (Barakat et al., *Biochem. J.* 388: 563-571, 2005). P-glycoprotein is associated with multi-drug resistance. Indeed, P-gp interacts with a wide variety of anti-cancer drugs leading to a decrease in their intracellular concentrations ultimately leading to failure of chemotherapy. P-glycoproteins have also been linked to neurological diseases. Indeed, neurological disorders including but not limited to epilepsy, Alzheimer's disease and Huntington's disease are associated with overexpression of ABC efflux transporters or substrates. Apart from their efflux transport activity, P-glycoproteins are also known to play a role in cellular migration and angiogenesis.

Given the involvement of P-gp substrates in disease, there is a need to develop therapeutic approaches aimed at regulating P-gp function, which can reduce the accumulation of P-gp substrates, can inhibit cellular migration or angiogenesis, or can treat neurological disorders and other diseases.

SUMMARY OF THE INVENTION

In a first aspect, the invention features a polypeptide including an amino acid sequence having at least 50% (e.g., at least 60%, 70%, 80%, 90%, 95%, 99%, or 100%) identity to the sequence DGIWKASFTTFTVTKYWFYR (SEQ ID NO: 1) or VTKYWFYR (SEQ ID NO: 2) or a peptide described in Table 1, where the polypeptide is less than 170 (e.g., less than 150, 125, 100, 75, 50, 40, 30, 25, 20, 15) amino acids in length. The polypeptide may be capable of interacting with (e.g., specifically binding) P-glycoprotein. In certain embodiments, a polypeptide having sequence identity to DGIWKASFTTFTVTKYWFYR (SEQ ID NO: 1) has a valine or leucine at the position corresponding to the thirteenth amino acid, has a tyrosine at the position corresponding to the sixteenth amino acid, has a lysine or arginine at the position corresponding to the twentieth amino acid, or any combination thereof. In other embodiments where the polypeptide has sequence identity to VTKYWFYR (SEQ ID NO: 2), the polypeptide has a valine or leucine at the position corresponding to the first amino acid, has a tyrosine at the position corresponding to the fourth amino acid, has a lysine or arginine at the position corresponding to the eighth amino acid, or any combination thereof. In some embodiments, the polypeptide is soluble or the polypeptide is substantially pure. The invention also features a composition including the polypeptide and a pharmaceutically acceptable carrier.

The invention also features a polypeptide including (a) an amino acid sequence having at least 50% (e.g., at least 60%, 70%, 80%, 90%, 95%, 99%, or 100%) identity to the sequence DGIWKASFTTFTVTKYWFYR (SEQ ID NO: 1) or VTKYWFYR (SEQ ID NO: 2), and (b) a heterologous sequence (e.g., any sequence described herein). The polypeptide may be capable of interacting with (e.g., specifically binding) P-glycoprotein. In some embodiments, the polypeptide is soluble or the polypeptide is substantially pure. The invention also features a composition including the polypeptide and a pharmaceutically acceptable carrier.

In another aspect, the invention features a soluble polypeptide including a fragment of caveolin-1 (e.g., any fragment described herein), where the fragment binds (e.g., specifically binds) to a portion of P-glycoprotein (e.g., amino acids 36-47 of P-glycoprotein). The invention also features a composition including the polypeptide and a pharmaceutically acceptable carrier.

In another aspect, the invention features a polypeptide including an amino acid sequence having at least 50% (e.g., at least 60%, 70%, 80%, 90%, 95%, 99%, or 100%) identity to the sequence VFSMFRYSNWLDK (SEQ ID NO: 3) or a peptide described in Table 2, where the peptide is less than 1000 (e.g., less than 750, 500, 250, 200, 150, 100, 90, 75, 60, 50, 40, 35, 30, 25, or 20) amino acids in length. The polypeptide may be capable of interacting with (e.g., specifically binding) caveolin-1. In certain embodiments, the peptide has a valine or leucine at the position corresponding to the first amino acid, has a tyrosine at the position corresponding to the seventh amino acid, has a lysine or arginine at the position corresponding to the thirteenth amino acid, or a combination thereof. In some embodiments, the polypeptide is soluble or the polypeptide is substantially pure. The invention also features a composition including the polypeptide and a pharmaceutically acceptable carrier.

In another aspect, the invention features a polypeptide including (a) an amino acid sequence having at least 50% (e.g., at least 60%, 70%, 80%, 90%, 95%, 99%, or 100%) identity to the sequence VFSMFRYSNWLDK (SEQ ID NO: 3), and (b) a heterologous sequence (e.g., any sequence described herein). The polypeptide may be capable of interacting with (e.g., specifically binding) caveolin-1. In some embodiments, the polypeptide is soluble or the polypeptide is substantially pure. The invention also features a composition including the polypeptide and a pharmaceutically acceptable carrier.

In another aspect, the invention features a soluble polypeptide including a fragment of P-glycoprotein, where the fragment binds to a portion of caveolin-1 (e.g., amino acids 82-101). In some embodiments, the polypeptide is soluble or the polypeptide is substantially pure. The invention also features a composition including the polypeptide and a pharmaceutically acceptable carrier.

In any of the above aspects, the polypeptide may differ from the sequence corresponding to either wild-type human caveolin-1 or human P-gp by at least a single amino substitution or deletion (e.g., 2, 3, 4, 5, 6, 7, 8, 9, 10 or more amino acid substitutions or deletions). In any of the above aspects, the polypeptide may include unnatural amino acid substitutions (e.g., those described herein) and may include peptidomimetics, such as those described herein. In certain embodiments, the polypeptide having a substitution or deletion may have increased (e.g., at least 5%, 10%, 25%, 50%, 75%, 100%, 200%, 500%, 1000%, 5000%, 10,000%, 50,000%) activity (e.g., P-gp efflux activity, stronger binding to either caveolin-1 or to P-gp). In certain embodiments, the polypeptide having a substitution or deletion exhibits decreased angiogenesis, or decreased or decreased cellular migration (e.g., at least 5%, 10%, 25%, 50%, 75%, 80%, 90%, 95%, or 99%) as compared to a polypeptide having the corresponding wild-type sequence.

In another aspect, the invention features a method of increasing P-gp-mediated efflux in a cell (e.g., in a patient), the method including administering a polypeptide of any of the previous aspects in an amount sufficient to increase P-gp-mediated efflux. In certain embodiments, the cell is in a patient. The patent may be suffering from a neoplasm (e.g., cancer) or from a neurological disease and the polypeptide may be administered in an amount sufficient to treat the neoplasm or the neurological disease. The neoplasm may be a cancer selected from the group consisting of leukemia, polycythemia vera, lymphoma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma. The neurological disease may be a neurodegenerative disease, which in turn, may be Alzheimer's disease, Parkinson's disease, Huntington's disease, prion disease, bovine spongiform encephalopathy, Creutzfeldt-Jakob disease, amyotrophic lateral sclerosis, Lewy body disease, or Pick's disease. In other embodiments, the patient is suffering from a disease or condition selected from the group consisting of drug intoxications (e.g., overdose), inclusion body myositis, cerebral amyloid angiopathy, amyloidosis (e.g., AA-type), and eye diseases (e.g., macular degeneration and glaucoma).

By "fragment" is meant a portion of a full length polypeptide sequence of at least 4, 5, 6, 7, 8, 10, 15, 20, 25, 40, 50, 60, 75, 90, 100, 125, 150, 200, 250, 300, 500, 750, or 1000 amino acids.

By "specifically binds" or "specific binding" is meant a compound (e.g., a polypeptide) or antibody that recognizes and binds a desired polypeptide but that does not substantially recognize and bind other molecules in a sample, for example, a biological sample. Binding may occur with a dissociation constant of at least 1000 µmol, 100 µmol, 10 µmol, 1 µmol, 100 nm, 10 nm, 1 nm, 100 pmol, 10 pmol, or 1 pmol.

By "substantially pure" or is meant a nucleic acid, polypeptide, or other molecule that has been separated from the components that naturally accompany it. Typically, a polypeptide is substantially pure when it is at least 30%, 40%, 50%, 60%, 70%, 80%, 90%, 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

By a "decrease" in the level of expression or activity of a gene or protein is meant a reduction in protein or nucleic acid level or activity in a cell, a cell extract, or a cell supernatant. For example, such a decrease may be due to inhibition by an exogenous compound RNA stability, transcription, or translation, increased protein degradation, or RNA interference. Preferably, this decrease is at least 5%, 10%, 25%, 50%, 75%, 80%, or even 90% of the level of expression or activity under control conditions. The decrease may be assayed by measuring changes in phenotypic response. In some embodiments, the decrease may be identified by measuring changes in angiogenesis or cell migration using, for example, the assays described herein.

By an "increase" in the expression or activity of a gene or protein is meant a positive change in protein or nucleic acid level or activity in a cell, a cell extract, or a cell supernatant. For example, such a increase may be due to competitive inhibition of an inhibitor, increased RNA stability, transcription, or translation, or decreased protein degradation. Preferably, this increase is at least 5%, 10%, 25%, 50%, 75%, 80%, 100%, 200%, or even 500% or more over the level of expression or activity under control conditions. The increase may be assayed by measuring changes in phenotypic response. In some embodiments, the increase may be identified by measuring changes in angiogenesis or cell migration using, for example, the assays described herein.

By "patient" is meant either a human or non-human animal (e.g., a mammal).

"Treating" a disease or condition in a subject or "treating" a patient having a disease or condition refers to subjecting the individual to a pharmaceutical treatment, e.g., the administration of a drug, such that at least one symptom of the disease or condition is decreased, stabilized, or prevented.

By "soluble" is meant soluble in aqueous solution under physiological conditions.

Other features and advantages of the invention will be apparent from the following Detailed Description, the drawings, and the claims.

BRIEF DESCRIPTION OF THE DRAWINGS

FIG. 5 depicts the amino acid sequences of human caveolin-1 (SEQ ID NO: 215) and human P-glycoprotein (SEQ ID NO: 214), with the binding regions shown in bold.

DETAILED DESCRIPTION

Figure 1A:
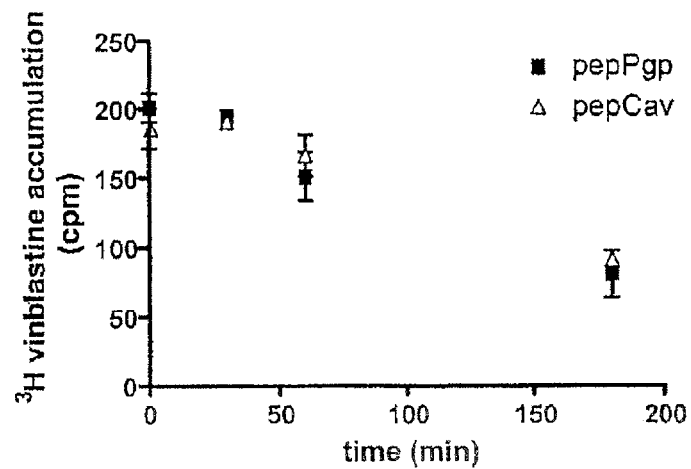
FIGS. 1A and 1B are graphs showing decreases in vinblastine accumulation in cells upon treatment with an exemplary pepPgp peptide (VFSMFRYSNWLDK (SEQ ID NO: 3)) or an exemplary pepCav peptide (DGIWKASFTTFTVTKYW- FYR (SEQ ID NO: 1)) over time (FIG. 1A) or using increasing pepPgp or pepCav concentrations (FIG. 1B).

P-glycoprotein is a membrane protein capable of transporting many different molecules from a cell. Caveolin-1, another membrane protein, is capable of interacting with P-gp and inhibits P-gp efflux activity. We, for the first time, have identified peptides derived from each of caveolin-1 and P-gp (e.g., pepCav and pepPgp) that are capable of blocking the caveolin-1/P-gp interaction (e.g., through competitive inhibition) and increasing the efflux activity of P-gp. Accordingly, the polypeptides of the invention may be useful in treatment of diseases (e.g., neurological diseases and neoplasms such as those described herein) where increased P-gp efflux is desired. In addition, we have shown that administration of these peptides decreases cellular migration and angiogenesis, thus indicating use of these peptides in treating neoplasms such as cancer.

Caveolin-1

Caveolin-1 is a 178 amino acid member of the caveolin family of proteins, which includes caveolin-1, -2, and -3. These proteins are typically found the caveolae, which are membrane invaginations found in many cell types. The caveolae are involved in endocytosis. Caveolin-1 interacts with many proteins (see, e.g., Table 2 of Razani et al., *Pharmacol. Rev.* 54:431-467, 2002, the entirety of which is hereby incorporated by reference) including P-gp (Jodoin et al., *J. Neurochem.* 87:1010-1023, 2003). Caveolin-1 is also involved in membrane transport, lipid, trafficking, and signal transduction. Caveolin-1 also forms homo-oligomers in cells. Caveolin-1 contains a scaffolding domain (amino acids residues 82-101), which is capable of binding P-gp (Demeule et al., *Vascul. Pharmacol.* 38:339-348, 2002). The scaffolding domain of caveolin-1 is involved in interactions with numerous proteins and was shown to negatively regulate some signaling molecules localized in caveolae, including eNOS, protein kinase C, and epidermal growth factor receptor (Okamoto et al., *J. Biol. Chem.* 273:5419-5422, 1998). In contrast to this, interaction of caveolin-1 with the insulin receptor increases insulin-stimulated phosphorylation of downstream targets (Yamamoto et al., *J. Biol. Chem.* 273: 26962-26968, 1998).

P-Glycoprotein

P-glycoprotein (P-gp) is a 1280 amino acid member of the ATP binding cassette (ABC) transporters and is capable of transporting compounds from cells. P-gp is encoded by the MDR1 gene; expression of this gene has been associated with multi-drug resistant cancer. Indeed P-gp is capable of transporting a variety of agents out of cells, including chemotherapeutic agents.

P-glycoprotein substrates may be endogenous and/or exogenous substances. These substrates encompass anticancer agents, immunosuppressive agents, HIV protease inhibitors, bioactive polypeptides, cardiac drugs, toxic peptides, and cytokines. Specific examples of P-gp substrates include beta-amyloid, taxol, taxol derivatives, cyclosporine A, vinblastine, vincristine, etoposide, doxorubicin, cyclophosphamide, taxotere, melphalan, chlorambucil, pharmaceutically acceptable salts and combination thereof as well as anticancer drugs such as vinca alkaloids, epipodophyllotoxins, anthracyclines, and taxanes that may be P-glycoprotein substrates among others as described by Turcotte et al., "The Blood-Brain Barrier: Roles of the Multidrug Resistance Transporter P-glycoprotein. Chapter 19 in Blood-Brain Interfaces: From Ontogeny to Artificial Interfaces. edited by R. Dermietzel, D. C. Spray and M. Nedergaard, Wiley-VCH, Weinheim, pp. 431-461, 2006.

P-gp activity has been linked to a number of disease states including neoplasms and neurological disorders. Here, we show that inhibition of P-gp activity results in decreased angiogenesis and cellular migration (see, e.g., the examples herein). In addition, polymorphisms in the P-gp gene have been associated with Parkinson's disease (PD) (Furuno et al., *Pharmacogenetics* 2:529-534, 2002). While P-gp expression is correlated with drug resistance in cancer cells, P-gp expression is down-regulated in neurological diseases, including Creutzfeldt-Jakob disease (CJD) (Vogelgesang et al., *Acta. Neuropathol.* (*Berl.*) 111:436-443, 2006). Further evidence of P-gp involvement in neurological diseases is shown by its ability to transport the amyloid-β peptide out of the brain (Lam et al., *J. Neurochem.* 76:1121-1128, 2001). Lowered expression or activity of P-gp at the blood-brain barrier may therefore be correlated with development of neurological diseases, and increasing P-gp activity may be useful to treat neurodegenerative diseases such as Alzheimer's disease, Parkinson's disease, amyotrophic lateral sclerosis (ALS), Huntington's disease, prion disease, bovine spongiform encephalopathy (BSE), CJD, Lewy body disease, and Pick's disease.

P-gp contains a consensus caveolin-binding motif that binds to the scaffolding domain of caveolin. Three related caveolin-binding motifs include ΦXΦXXXXΦ (SEQ ID NO: 4), ΦXXXXΦXXΦ (SEQ ID NO: 5) and ΦXΦXXXX-ΦXXΦ (SEQ ID NO: 6), where Φ is a phenylalanine, tyrosine, or tryptophan and X is any amino acid.

Consensus Binding Domains

An exemplary sequence derived from the cholesterol binding sequence localized on caveolin-1, DGIWKASFTTFTVT-KYWFYR (SEQ ID NO: 1). An exemplary sequence derived from the P-gp protein is VFSMFRYSNWLDK (SEQ ID NO: 3), the P-gp cholesterol binding sequence. Both of these exemplary sequences conform to the cholesterol binding consensus motif:

L/V-A2-Y-A3-K/R (SEQ ID NO: 7)

where each of A2 and A3 independently represents between one and five amino acids. The amino acids may be any naturally occurring amino acids (e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine) or any modified or non-naturally occurring amino acids (e.g., those described herein).

Accordingly, peptides of the invention can have the formula:

A1-L/V-A2-Y-A3-K/R-A4 (SEQ ID NO: 8)

and may be capable of stimulating P-glycoprotein efflux, transport activity, or may inhibit cellular migration and/or angiogenesis. A1 may be absent or an amino acid sequence of 1 to about 19 amino acids; A2 is an amino acid sequence consisting of 1 to 5 amino acids; A3 is an amino acid sequence consisting of 1 to 5 amino acids and A4 may be absent or an amino acid sequence of 1 up to about 19 amino acids. Each amino acid may be any amino acid (e.g., any of those described herein).

Caveolin-1 Fragments

We have identified the exemplary fragments DGIWKASFTTFTVTKYWFYR (SEQ ID NO: 1) and VTKYWFYR (SEQ ID NO: 2) derived from the caveolin-1 sequence as being capable of enhancing P-gp efflux activity. On this basis, the invention provides polypeptides including these fragments. The polypeptides of the invention may include an amino acid sequence with at least 50%, 60%, 70%, 80%, 85%, 90%, 95%, 99%, or 100% identity to a fragment of the caveolin-1 sequence. Preferred polypeptides are soluble under physiological conditions or can bind to P-glycoprotein and increase its efflux activity. Exemplary fragments are shown in Table 1. In certain embodiments, the polypeptide includes the fragment DGIWKASFTTFTVTKYWFYR (SEQ ID NO: 1) or VTKYWFYR (SEQ ID NO: 2), or portions thereof (see e.g., Table 1). Polypeptides of the invention may also include additional portions of the caveolin-1 sequence (e.g., at least 1, 2, 3, 4, 6, 7, 10, 15, 20, 25, 30, 40, 50, 60, 75, 90, 100 additional amino acids at the N-terminal of the fragment, the C-terminal of the fragment, or both). Polypeptides of the invention can also include heterologous sequences (e.g., as described herein). In some embodiments, the polypeptides of the invention may include tandem repeats (e.g., at least 2, 3, 5, 8, 10, or 15 repeats) of a P-gp fragment.

TABLE 1

Exemplary caveolin-1 fragments

| fragment | SEQ ID NO: | fragment | SEQ ID NO: | fragment | SEQ ID NO: | fragment | SEQ ID NO: |
|---|---|---|---|---|---|---|---|
| DGIWKASFTTFTVTKYWFYR | 1 | ASFTTFTVTKYW | 9 | VTKYWFYR | 2 | WKASFT | 10 |
| GIWKASFTTFTVTKYWFYR | 11 | KASFTTFTVTKY | 12 | TVTKYWFY | 13 | IWKASF | 14 |
| DGIWKASFTTFTVTKYWFY | 15 | WKASFTTFTVTK | 16 | FTVTKYWF | 17 | GIWKAS | 18 |
| IWKASFTTFTVTKYWFYR | 19 | IWKASFTTFTVT | 20 | TFTVTKYW | 21 | DGIWKA | 22 |
| GIWKASFTTFTVTKYWFY | 23 | GIWKASFTTFTV | 24 | TTFTVTKY | 25 | YWFYR | 26 |
| DGIWKASFTTFTVTKYWF | 27 | DGIWIKASFTTFT | 28 | FTTFTVTK | 29 | KYWFY | 30 |
| WKASFTTFTVTKYWFYR | 31 | TFTVTKYWFYR | 32 | SFTTFTVT | 33 | TKYWF | 34 |
| IWKASFTTFTVTKYWFY | 35 | TTFTVTKYWFY | 36 | ASFTFTV | 37 | VTKYW | 38 |
| GIWKASFTTFTVTKYWF | 39 | FTTFTVTKYWF | 40 | KASFTTFT | 41 | TVTKY | 42 |
| DGIWKASFTTFTVTKYW | 43 | SFTTFTVTKYW | 44 | WKASFTTF | 45 | FTVTK | 46 |
| KASFTTFTVTKYWFYR | 47 | ASFTTFTVTKY | 48 | IWKASFTT | 49 | TFTVT | 50 |
| WKASFTTFTVTKYWFY | 51 | KASFTTFTVTK | 52 | GIWKASFT | 53 | TTFTV | 54 |
| IWKASFTTFTVTKYWF | 55 | WKASFTTFTVT | 56 | DGIWKASF | 57 | FTTFT | 58 |
| GIWKASFTTFTVTKYW | 59 | IWKASFTTFTV | 60 | TKYWFYR | 61 | SFTTF | 62 |
| DGIWKASFTTFTVTKY | 63 | GIWKASFTTFT | 64 | VTKYWFY | 65 | ASFTT | 66 |
| ASFTTFTVTKYWFYR | 67 | DGIWKASFTTF | 68 | TVTKYWF | 69 | KASFT | 70 |
| KASFTTFTVTKYWFY | 71 | FTVTKYWFYR | 72 | FTVTKYW | 73 | WKASF | 74 |
| WKASFTTFTVTKYWF | 75 | TFTVTKYWFY | 76 | TFTVTKY | 77 | IWKAS | 78 |
| IWKASFTTFTVTKYW | 79 | TTFTVTKYWF | 80 | TTFTVTK | 81 | GIWKA | 82 |
| GIWKASFTTFTVTKY | 83 | FTTFTVTKYW | 84 | FTTFTVT | 85 | DGIWK | 86 |
| DGIWKASFTTFTVTK | 87 | SFTTFTVTKY | 88 | SFTTFTV | 89 | WFYR | 90 |
| SFTTFTVTKYWFYR | 91 | ASFTTFTVTK | 92 | ASFTTFT | 93 | YWFY | 94 |
| ASFTTFTVTKYWFY | 95 | KASFTTFTVT | 96 | KASFTTF | 97 | KYWF | 98 |
| KASFTTFTVTKYWF | 99 | WKASFTTFTV | 100 | WKASFTT | 101 | TKYW | 102 |
| WKASFTTFTVTKYW | 103 | IWKASFTTFT | 104 | IWKASFT | 105 | VTKY | 106 |

TABLE 1-continued

Exemplary caveolin-1 fragments

| fragment | SEQ ID NO: | fragment | SEQ ID NO: | fragment | SEQ ID NO: | fragment | SEQ ID NO: |
|---|---|---|---|---|---|---|---|
| IWKASFTTFTVTKY | 107 | GIWKASFTTF | 108 | GIWKASF | 109 | TVTK | 110 |
| GIWKASFTTFTVTK | 111 | DGIWKASFTT | 112 | DGIWKAS | 113 | FTVT | 114 |
| DGIWKASFTTFTVT | 115 | TVTKYWFYR | 116 | KYWFYR | 117 | TFTV | 118 |
| FTTFTVTKYWFYR | 119 | FTVTKYWFY | 120 | TKYWFY | 121 | TTFT | 122 |
| SFTTFTVTKYWFY | 123 | TFTVTKYWF | 124 | VTKYWF | 125 | FTTF | 126 |
| ASFTTFTVTKYWF | 127 | TTFTVTKYW | 128 | TVTKYW | 129 | SFTT | 130 |
| KASFTTFTVTKYW | 131 | FTTFTVTKY | 132 | FTVTKY | 133 | ASFT | 134 |
| WKASFTTFTVTKY | 135 | SFTTFTVTK | 136 | TFTVTK | 137 | KASF | 138 |
| IWKASFTTFTVTK | 139 | ASFTTFTVT | 140 | TTFTVT | 141 | WKAS | 142 |
| GIWKASFTTFTVT | 143 | KASFTTFTV | 144 | FTTFTV | 145 | IWKA | 146 |
| DGIWKASFTTFTV | 147 | WKASFTTFT | 148 | SFTTFT | 149 | GIWK | 150 |
| TTFTVTKYWFYR | 151 | IWKASFTTF | 152 | ASFTTF | 151 | DGIW | 154 |
| FTTFTVTKYWFY | 155 | GIWKASFTT | 156 | KASFTT | 157 | | |
| SFTTFTVTKYWF | 158 | DGIWKASFT | 159 | | | | |

Deletion analysis can be used to determine the minimal peptide sequence required for the interaction with P-gp or required to increase P-gp-mediated efflux. Deletion fragments (e.g., with 1, 2, 3, 4, 5, 6, 7, 8, 9, 10, 11, 12, 13, 14, 15, or 16 amino acids deleted from the N-terminal, from the C-terminal, or from a combination thereof) of the DGIWKASFTTFTVTKYWFYR (SEQ ID NO: 1) fragment can be generated using molecular biological methods known in the art and assayed for binding to P-gp or for increases in P-gp activity (see, e.g., the methods described below).

P-Glycoprotein Fragments

We have identified the exemplary fragment VFSMFRYSNWLDK (SEQ ID NO: 3) derived from the P-gp sequence (amino acids 36-48) as binding caveolin-1 and capable of enhancing P-gp efflux activity. On this basis, the invention provides polypeptides including these fragments. The polypeptides of the invention may include an amino acid sequence with at least 50%, 60%, 70%, 80%, 85%, 90%, 95%, 99%, or 100% identity to a fragment (e.g., the fragments described herein) of the P-gp sequence. Preferred polypeptides are soluble under physiological conditions, can bind to caveolin-1, or can increase P-gp efflux activity. Exemplary fragments are shown in Table 2. In certain embodiments, the polypeptide includes the fragment VFSMFRYSNWLDK (SEQ ID NO: 3), or portions thereof (see e.g., Table 2). Polypeptides of the invention may also include additional portions of the P-gp sequence (e.g., at least 1, 2, 3, 4, 6, 7, 10, 15, 20, 25, 30, 40, 50, 60, 75, 90, 100, 200, 300, 400, 500, or 600 additional amino acids at the N-terminal of the fragment, the C-terminal of the fragment, or both). Polypeptides of the invention can also include heterologous sequences (e.g., as described herein). In some embodiments, the polypeptides of the invention may include tandem repeats (e.g., at least 2, 3, 5, 8, 10, or 15 repeats) of a P-gp fragment.

TABLE 2

P-glycoprotein fragments

| fragment | SEQ ID NO: | fragment | SEQ ID NO: | fragment | SEQ ID NO: |
|---|---|---|---|---|---|
| VFSMFRYSNWLDK | 3 | FSMFRYSN | 160 | SNWLD | 161 |
| FSMFRYSNWLDK | 162 | VFSMFRYS | 163 | YSNWL | 164 |
| VFSMFRYSNWLD | 165 | YSNWLDK | 166 | RYSNW | 167 |
| SMFRYSNWLDK | 168 | RYSNWLD | 169 | FRYSN | 170 |
| FSMFRYSNWLD | 171 | FRYSNWL | 172 | MFRYS | 173 |
| VFSMFRYSNWL | 174 | MFRYSNW | 175 | SMFRY | 176 |
| MFRYSNWLDK | 177 | SMFRYSN | 178 | FSMFR | 179 |
| SMFRYSNWLD | 180 | FSMFRYS | 181 | VFSMF | 182 |
| FSMFRYSNWL | 183 | VFSMFRY | 184 | WLDK | 185 |
| VFSMFRYSNW | 186 | SNWLDK | 187 | NWLD | 188 |
| FRYSNWLDK | 189 | YSNWLD | 190 | SNWL | 191 |
| MFRYSNWLD | 192 | RYSNWL | 193 | YSNW | 194 |
| SMFRYSNWL | 195 | FRYSNW | 196 | RYSN | 197 |
| FSMFRYSNW | 198 | MFRYSN | 199 | FRYS | 200 |
| VFSMFRYSN | 201 | SMFRYS | 202 | MFRY | 203 |
| RYSNWLDK | 204 | FSMFRY | 205 | SMFR | 206 |

TABLE 2-continued

P-glycoprotein fragments

| fragment | SEQ ID NO: | fragment | SEQ ID NO: | fragment | SEQ ID NO: |
|---|---|---|---|---|---|
| FRYSNWLD | 207 | VFSMFR | 208 | FSMF | 209 |
| MFRYSNWL | 210 | NWLDK | 211 | VFSM | 212 |
| SMFRYSNW | 213 | | | | |

As with the caveolin-1 fragments, deletion analysis can also be used to determine the minimal peptide sequence required for the interaction of the P-gp fragments with caveolin-1 or the minimal peptide sequence required to increase P-gp-mediated efflux (e.g., using the assays described herein). Deletion fragments (e.g., with 1, 2, 3, 4, 5, 6, 7, 8, 9, 10, 11, 12, 13, 14, 15, or 16 amino acids deleted from the N-terminal, from the C-terminal, or a combination thereof) of the VFSMFRYSNWLDK (SEQ ID NO: 3) fragment can be generated using molecular biologic methods known in the art and assayed for binding to caveolin-1 or assayed for increases in P-gp activity (see, e.g., the methods described below).

Fusion Proteins

The polypeptides of the invention include fusion proteins (e.g., a fragment of caveolin-1 or P-gp and a heterologous sequence). The caveolin-1 or P-gp portion of the fusion protein may be soluble (e.g., lacking the transmembrane domains) or may be any functional fragment of caveolin-1 or P-gp (e.g., a fragment capable of regulating efflux activity of P-gp). The caveolin-1 or P-gp portion of the fusion protein may be at least 70%, 75%, 80%, 85%, 90%, 95%, 99%, or 100% identical to at least a portion (e.g., any portion described herein) of the full length caveolin-1 or P-gp protein (e.g., the human protein).

The caveolin-1 or P-gp fragment may be fused to one or more fusion partners at either its N-terminus or C-terminus. In certain embodiments, one of the fusion partners is the Fc protein (e.g., mouse Fc or human Fc). In other embodiments, the heterologous sequence may be a purification or detection tag, for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides (e.g., preprotyrypsin signal sequence). In other embodiments the fusion partner may be a tag, such as c-myc, poly histidine, or FLAG. Each fusion partner may contain one or more domains, e.g., a preprotrypsin signal sequence and FLAG tag.

The fusion proteins may include additional amino acid residues (e.g., at least 1, 2, 3, 4, 5, 8, 10, 12, 15, 20, 25, 40, 50, 75, 100) at either the N or C terminus (e.g., 1 to 10, 1 to 11, 1 to 12, 1 to 13, 1 to 14, 1 to 15, 1 to 16, 1 to 17 1 18, and 1 to 19 amino acids).

Peptide Modifications

Peptides having a modification can be employed in the invention. Such modifications include may maintain or increase the biological activity of the original polypeptide or may optimize one or more of the particularity (e.g. stability, bioavailability, etc.) of the compounds of the invention. Polypeptides of the invention may include for example, amino acid sequences modified either by natural processes, such as posttranslational processing, or by chemical modification techniques which are known in the art. Modifications may occur anywhere in a polypeptide including the polypeptide backbone, the amino acid side-chains and the amino- or carboxy-terminus. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched, and branched cyclic polypeptides may result from posttranslational natural processes or may be made by synthetic methods. Other modifications include, for example, pegylation, acetylation, acylation, addition of acetomidomethyl (Acm) group, ADP-ribosylation, alkylation. amidation, biotinylation, carbamoylation, carboxyethylation, esterification, covalent attachment to flavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination. In addition, polypeptides of the invention may include more than one modification.

Polypeptides of the invention may also include substitutions of non naturally occurring amino acids. A non-naturally occurring amino acid is to be understood herein as an amino acid which is not naturally produced or found in a mammal. Non-naturally occurring amino acids include D-amino acids, amino acids having an acetylaminomethyl group attached to a sulfur atom of a cysteine, a pegylated amino acid. Non-naturally occurring amino acids also include omega amino acids of the formula $NH_2(CH_2)_nCOOH$ where n is 2-6, sarcosine, t-butyl alanine, t-butyl glycine, N-methyl isoleucine, norleucine, and phenylglycine (e.g., a substitute for Trp, Tyr or Phe). Other amino acids include citrulline, methionine sulfoxide, cysteic acid, ornithine, hydroxyproline (e.g., in place of proline).

Preparation of Peptide Derivatives and Peptidomimetics

In addition to peptides consisting only of naturally occurring amino acids, peptidomimetics or peptide analogs are also encompassed by the present invention. Peptide analogs are commonly used in the pharmaceutical industry as non-peptide drugs with properties analogous to those of the template peptide. The non-peptide compounds are termed "peptide mimetics" or peptidomimetics (Fauchere et al., *Infect. Immun.* 54:283-287, 1986; Evans et al., *J. Med. Chem.* 30:1229-1239, 1987). Peptide mimetics that are structurally related to therapeutically useful peptides may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —$CH_2NH$—, —$CH_2S$—, —$CH_2$—$CH_2$—, —$CH$=$CH$— (cis and trans), —$CH_2SO$—, —$CH(OH)CH_2$—, —$COCH_2$— etc., by methods well known in the art (Spatola, *Peptide Backbone Modifications, Vega Data,* 1(3):267, 1983); Spatola et al. (*Life Sci.* 38:1243-1249, 1986); Hudson et al. (*Int. J. Pept. Res.* 14:177-185, 1979); and Weinstein. B., 1983, Chemistry and Biochemistry, of Amino Acids, Peptides and Proteins, Weinstein eds, Marcel Dekker, New-York). Such peptide mimetics may have significant advantages over naturally-occurring polypeptides including more economical production, greater chemical stability, enhanced pharmacological properties (e.g., half-life, absorption, potency, efficiency), reduced antigenicity and others.

While peptides are effective in stimulating P-gp-mediated efflux in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., Pharm. Res. 10:1268-1273, 1993). In light of this, it is often advantageous to use modified versions of peptides. The modified peptides retain the structural characteristics of the original L-amino acid peptides that confer biological activity with regard to IGF-1, but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide. The presence of an N-terminal or C-terminal D-amino acid increases the in vivo stability of a peptide since peptidases cannot utilize a D-amino acid as a substrate (Powell et al., Pharm. Res. 10:1268-1273, 1993). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same tertiary conformation and therefore the same activity, as the L-amino acid peptides, but are more stable to enzymatic degradation in vitro and in vivo, and thus have greater therapeutic efficacy than the original peptide (Brady and Dodson, Nature 368: 692-693, 1994; Jameson et al., Nature 368:744-746, 1994). In addition to reverse-D-peptide, constrained peptides comprising a consensus sequence or a substantially identical consensus sequence variation may be generated by methods well known in the art (Rizo and Gierasch, Ann. Rev. Biochem. 61:387-418, 1992). For example, constrained peptides may be generated by adding cysteine residues capable of forming disulfide bridges and, thereby, resulting in a cyclic peptide. Cyclic peptides have no free N- or C-termini. Accordingly, they are not susceptible to proteolysis by exopeptidases, although they are, of course, susceptible to endopeptidases, which do not cleave at peptide termini. The amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

A cyclic derivative containing an intramolecular disulfide bond may be prepared by conventional solid phase synthesis while incorporating suitable S-protected cysteine or homocysteine residues at the positions selected for cyclization such as the amino and carboxy termini (Sah et al., J. Pharm. Pharmacol. 48:197, 1996). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure or (2) by removal of the peptide from the support along with complete side chain de-protection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S-alkyl bonds can be prepared by conventional solid phase chemistry while incorporating an amino acid residue with a suitable amino-protected side chain, and a suitable S-protected cysteine or homocysteine residue at the position selected for cyclization.

Another effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., Pharm. Res. 10:1268-1273, 1993). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

Also included by the present invention are other types of peptide derivatives containing additional chemical moieties not normally part of the peptide, provided that the derivative retains the desired functional activity of the peptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives.

Longer peptide sequences which result from the addition of additional amino acid residues to the peptides of the invention are also encompassed in the present invention. Such longer peptide sequence would be expected to have the same biological activity (e.g., binding to and stimulating P-gp-mediated efflux) as the peptides described above. While peptides having a substantial number of additional amino acids are not excluded, it is recognized that some large polypeptides may assume a configuration that masks the effective sequence, thereby preventing binding to the target (e.g., caveolin-1 or P-gp). These derivatives could act as competitive antagonists. Thus, while the present invention encompasses peptides or derivatives of the peptides described herein having an extension, desirably the extension does not destroy the P-gp efflux stimulatory activity of the peptide or derivative.

Other derivatives included in the present invention are dual peptides consisting of two of the same, or two different peptides of the present invention covalently linked to one another either directly or through a spacer, such as by a short stretch of alanine residues or by a putative site for proteolysis (e.g., by cathepsin, see e.g., U.S. Pat. No. 5,126,249 and European Patent No. 495 049). Multimers of the peptides of the present invention consist of polymer of molecules formed from the same or different peptides or derivatives thereof.

The present invention also encompasses peptide derivatives that are chimeric or fusion proteins containing a peptide described herein, or fragment thereof, linked at its amino- or carboxy-terminal end, or both, to an amino acid sequence of a different protein. Such a chimeric or fusion protein may be produced by recombinant expression of a nucleic acid encoding the protein. For example, a chimeric or fusion protein may contain at least 6 amino acids of a peptide of the present invention and desirably has a functional activity equivalent or greater than a peptide of the invention.

Peptide derivatives of the present invention can be made by altering the amino acid sequences by substitution, addition, or deletion or an amino acid residue to provide a functionally equivalent molecule, or functionally enhanced or diminished molecule, as desired. The derivative of the present invention include, but are not limited to, those containing, as primary amino acid sequence, all or part of the amino acid sequence of the peptides described herein (e.g., a VEGFR peptide 2.1, 2.2, or 2.3, or an APG-201, APG-202, APG-203, APG-204, APG-205, or APG-206 peptide, or an API-101, API-103, or API-106 peptide, or an API-401, API-402, API-403, API-404, or API-405 peptide) including altered sequences containing substitutions of functionally equivalent amino acid residues. For example, one or more amino acid residues within the sequence can be substituted by another amino acid of a similar polarity which acts as a functional equivalent, resulting in a silent alteration. Substitution for an amino acid within the sequence may be selected from other members of the class to which the amino acid belongs. For example, the positively charged (basic) amino acids include, arginine, lysine and histidine. The nonpolar (hydrophobic) amino acids include, leucine, isoleucine, alanine, phenylalanine, valine, proline, tryptophane and methionine. The uncharged polar amino acids include serine, threonine, cysteine, tyrosine, asparagine and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions.

Assays to Identify Peptidomimetics

As described above, non-peptidyl compounds generated to replicate the backbone geometry and pharmacophore display (peptidomimetics) of the peptides identified by the methods of the present invention often possess attributes of greater metabolic stability, higher potency, longer duration of action and better bioavailability.

The peptidomimetics compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, *Anticancer Drug Des.* 12:145, 1997). Examples of methods for the synthesis of molecular libraries can be found in the art, for example, in: DeWitt et al. (*Proc. Natl. Acad. Sci. USA* 90:6909, 1993); Erb et al. (*Proc. Natl. Acad. Sci. USA* 91:11422, 1994); Zuckermann et al., *J. Med. Chem.* 37:2678, 1994); Cho et al. (*Science* 261:1303, 1993); Carell et al. (*Angew. Chem, Int. Ed. Engl.* 33:2059, 1994 and ibid 2061); and in Gallop et al. (*Med. Chem.* 37:1233, 1994). Libraries of compounds may be presented in solution (e.g., Houghten, *Biotechniques* 13:412-421, 1992) or on beads (Lam, *Nature* 354:82-84, 1991), chips (Fodor, *Nature* 364:555-556, 1993), bacteria or spores (U.S. Pat. No. 5,223,409), plasmids (Cull et al., *Proc. Natl. Acad. Sci. USA* 89:1865-1869, 1992) or on phage (Scott and Smith, *Science* 249:386-390, 1990), or luciferase, and the enzymatic label detected by determination of conversion of an appropriate substrate to product.

Once a peptide of the present invention is identified, it may be isolated and purified by any number of standard methods including, but not limited to, differential solubility (e.g., precipitation), centrifugation, chromatography (e.g., affinity, ion exchange, size exclusion, and the like) or by any other standard techniques used for the purification of peptides, peptidomimetics or proteins. The functional properties of an identified peptide of interest may be evaluated using any functional assay known in the art. Desirably, assays for evaluating downstream receptor function in intracellular signaling are used (e.g., cell proliferation).

For example, the peptidomimetics compounds of the present invention may be obtained using the following three-phase process: (1) scanning the peptides of the present invention to identify regions of secondary structure necessary for recognition and activity toward either caveolin-1 or P-gp; (2) using conformationally constrained dipeptide surrogates to refine the backbone geometry and provide organic platforms corresponding to these surrogates; and (3) using the best organic platforms to display organic pharmocophores in libraries of candidates designed to mimic the desired activity of the native peptide. In more detail the three phases are as follows. In phase 1, the lead candidate peptides are scanned and their structure abridged to identify the requirements for their activity. A series of peptide analogs of the original are synthesized. In phase 2, the best peptide analogs are investigated using the conformationally constrained dipeptide surrogates. Indolizidin-2-one, indolizidin-9-one and quinolizidinone amino acids ($I^2$aa, $I^9$aa and Qaa respectively) are used as platforms for studying backbone geometry of the best peptide candidates. These and related platforms (reviewed in Halab et al., *Biopolymers* 55:101-122, 2000; and Hanessian et al. *Tetrahedron* 53:12789-12854, 1997) may be introduced at specific regions of the peptide to orient the pharmacophores in different directions. Biological evaluation of these analogs identifies improved lead peptides that mimic the geometric requirements for activity. In phase 3, the platforms from the most active lead peptides are used to display organic surrogates of the pharmacophores responsible for activity of the native peptide. The pharmacophores and scaffolds are combined in a parallel synthesis format. Derivation of peptides and the above phases can be accomplished by other means using methods known in the art.

Structure function relationships determined from the peptides, peptide derivatives, peptidomimetics or other small molecules of the present invention may be used to refine and prepare analogous molecular structures having similar or better properties. Accordingly, the compounds of the present invention also include molecules that share the structure, polarity, charge characteristics and side chain properties of the peptides described herein.

In summary, based on the disclosure herein, those skilled in the art can develop peptides and peptidomimetics screening assays which are useful for identifying compounds for interacting with and stimulating P-gp-mediated efflux. The assays of this invention may be developed for low-throughput, high-throughput, or ultra-high throughput screening formats. Assays of the present invention include assays which are amenable to automation.

Identification of Additional P-gp Inhibitory Peptides

Additional peptides that inhibit P-gp efflux (e.g., derived from caveolin-1 or from P-gp) can be identified using the methods described herein or any other assays that can be used to measure P-gp activity known in the art. In certain embodiments, the test peptide is used in the cellular migration or the angiogenesis (e.g., in vivo or in vitro) assays described herein (see, e.g., Examples 4-6). In these embodiments, a test peptide is contacted with cells or an organism expressing P-gp. Migration or blood vessel formation is measured in the presence or absence of these peptides. A decrease in either cellular migration or angiogenesis in the presence of the test peptide as compared to in the absence of the peptide identifies the test peptide as a P-gp-inhibitory peptide.

In other embodiments, efflux of a compound (e.g., vinblastine or TAXOL) in a cell expressing P-gp can be measured (see, e.g., Examples 1-3). Any compound known to be transported by P-gp can be used in these assays. The compound may be detectably labeled using any label known in the art (e.g., those described herein). In these exemplary methods, efflux of a compound is compared in the presence and absence of a test peptide, where increased efflux of the compound in the presence of the test peptide is indicative of the peptide having P-gp-stimulatory activity.

Other approaches, including in vitro binding assays, may be used to identify candidate peptides. In one particular embodiment, a test peptide that binds to P-gp or caveolin-1 or a portion thereof may be identified using a chromatography-based technique. For example, recombinant or synthetic fragments of either P-gp or caveolin-1 may be produced and purified by standard techniques and may be immobilized on a column. A test peptide or group of test peptides is then passed through the column, and a peptide specific for the bound P-gp or caveolin-1 fragment is identified on the basis of its ability to bind to the polypeptide and be immobilized on the column. To isolate the test peptide, the column is washed to remove non-specifically bound molecules, and the peptide of interest is then released from the column and collected. Peptides isolated by this method (or any other appropriate method) may, if desired, be further purified (e.g., by high performance liquid chromatography). Peptides isolated by this approach may also be used, for example, as therapeutics to treat a disorder in which P-gp efflux is decreased (e.g., any of those described herein). Compounds which are identified as binding with an affinity constant less than or equal to 10 mM are considered particularly useful in the invention.

Nucleic Acids

The present invention also includes nucleic acids encoding any of the polypeptides described herein. In some embodiments, the polynucleotide may be included in a vector suitable for expression of the polypeptide in a cell or in an organism (e.g., useful for gene therapy or protein expression as described below).

Polypeptide Expression

In general, polypeptides of the invention may be produced by transformation of a suitable host cell with all or part of a polypeptide-encoding polynucleotide molecule or fragment thereof in a suitable expression vehicle.

Those skilled in the field of molecular biology will understand that any of a wide variety of expression systems may be used to provide the recombinant polypeptide. The precise host cell used is not critical to the invention. A polypeptide of the invention may be produced in a prokaryotic host (e.g., E. coli) or in a eukaryotic host (e.g., Saccharomyces cerevisiae, insect cells, e.g., Sf21 cells, or mammalian cells, e.g., NIH 3T3, HeLa, or preferably COS or CHO cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (Pouwels, P. H. et al., 1985, Supp. 1987).

One particular bacterial expression system for polypeptide production is the E. coli pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains which express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system which is designed for high-level expression of genes or gene fragments as fusion proteins with rapid purification and recovery of functional gene products. The polypeptide of interest is fused to the carboxyl terminus of the glutathione S-transferase protein from Schistosoma japonicum and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, polypeptides expressed in pGEX-2T plasmids may be cleaved with thrombin; those expressed in pGEX-3X may be cleaved with factor Xa.

Once isolated, the recombinant polypeptide can, if desired, be further purified, e.g., by high performance liquid chromatography (see, e.g., Fisher, Laboratory Techniques In Biochemistry And Molecular Biology, eds., Work and Burdon, Elsevier, 1980).

Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.).

These general techniques of polypeptide expression and purification can also be used to produce and isolate useful peptide fragments or analogs (described herein). In certain embodiments, a combination of techniques may be used to generate the fusion protein. For example, the protein and its fusion partner may be produced recombinantly and purified, or may be purified from a natural source, and then chemically coupled together to form the fusion protein.

Treatment Methods of the Invention

A polypeptide of the invention or polynucleotide encoding an polypeptide of the can be administered to a mammal (e.g., a human) suffering from any P-gp associated disorder. These disorders include any neoplasm such as a cancer, any neurological disorder such as a neurodegenerative disorder (e.g., those described herein), or any other disease described herein.

The polypeptide or polynucleotide may be administered by any route known in the art or described herein, for example, oral, parenteral (e.g., intravenously or intramuscularly), intraperitoneal, rectal, cutaneous, nasal, vaginal, inhalant, skin (patch), or ocular. The polypeptide or polynucleotide may be administered in any dose or dosing regimen (e.g., those described herein).

Dosage

With respect to the therapeutic methods of the invention, it is not intended that the administration of the polypeptide or polynucleotide encoding such a protein be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat the P-gp-related disorder. The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, therapeutically effective amounts of the polypeptides of the invention protein may provided at a dose of 0.0001, 0.01, 0.01 0.1, 1, 5, 10, 25, 50, 100, 500, or 1,000 mg/kg.

Diseases

The polypeptides of the invention may be used to treat any disease where inhibition of the interaction between caveolin-1 and P-gp is desired or increased P-gp efflux is desired. As we have shown that the exemplary peptides pepCav and pepPgp are capable of decreasing angiogenesis and cellular migration, the polypeptides of the invention may be used to treat any neoplasm such as cancer. Exemplary cancers include leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma.

In addition, neurological diseases, such as neurodegenerative diseases, may also be associated with decreased P-gp activity. Patient suffering from, or at increased risk of developing, a neurological disease (e.g., the neurodegenerative diseases described herein) may therefore benefit from increased P-gp activity. Accordingly, the polypeptides of the invention may be used to treat patients suffering from diseases such as AD, PD, Huntington's disease, Prion disease, bovine spongiform encephalopathy, CJD, ALS, Lewy body disease, or Pick's disease.

Other diseases that can be treated with the polypeptides of the invention include drug intoxications (e.g., overdose), inclusion body myositis, cerebral amyloid angiopathy, amyloidosis (e.g., AA-type), and eye diseases (e.g., macular degeneration and glaucoma).

Formulation of Pharmaceutical Compositions

The administration of an polypeptide or polynucleotide may be by any suitable means that results in a concentration of the protein that treats the disorder. The compound may be contained in any appropriate amount in any suitable carrier substance, and is generally present in an amount of 1-95% by weight of the total weight of the composition. The composition may be provided in a dosage form that is suitable for the oral, parenteral (e.g., intravenously or intramuscularly), intraperitoneal, rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy*, 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions according to the invention may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agent(s) of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the therapeutic to a particular target cell type. Administration of the protein in the form of a controlled release formulation is especially preferred for compounds having a narrow absorption window in the gastrointestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the protein is formulated with appropriate excipients into a pharmaceutical composition that, upon administration, releases the protein in a controlled manner. Examples include single or multiple unit tablet or capsule compositions, oil solutions, suspensions, emulsions, microcapsules, molecular complexes, microspheres, nanoparticles, patches, and liposomes.

Parenteral Compositions

The pharmaceutical composition may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. The composition may also be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine), poly(lactic acid), polyglycolic acid, and mixtures thereof. Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)) or combinations thereof.

Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the protein in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in Encyclopedia of Pharmaceutical Technology, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil.

Powders and granulates may be prepared using the ingredients mentioned above under tablets and capsules in a conventional manner using, e.g., a mixer, a fluid bed apparatus, or spray drying equipment.

Gene Therapy

A polypeptide of the invention can be effectively administered to a cell or patient using gene therapy techniques. See, generally, for example, U.S. Pat. No. 5,399,346. The general principle is to introduce the polynucleotide into a target cell in a patient, and allow it to express a polypeptide that enhances the activity of the endogenous P-gp protein.

Entry into the cell is facilitated by suitable techniques known in the art such as providing the polynucleotide in the form of a suitable vector, or encapsulation of the polynucleotide in a liposome.

A desired mode of gene therapy is to provide the polynucleotide in such a way that it will replicate inside the cell, enhancing and prolonging the desired effect. Thus, the polynucleotide is operably linked to a suitable promoter, such as the natural promoter of the corresponding gene, a heterologous promoter that is intrinsically active in liver, neuronal, bone, muscle, skin, joint, or cartilage cells, or a heterologous promoter that can be induced by a suitable agent.

EXAMPLES

The following examples illustrate potential applications of the invention and are not intended to limit scope. Modifications and variations may be made therein without departing from the spirit and scope of the invention.

Example 1

Stimulation of the P-gp Efflux Transport Activity of Vinblastine in Vitro

Figure 1B:
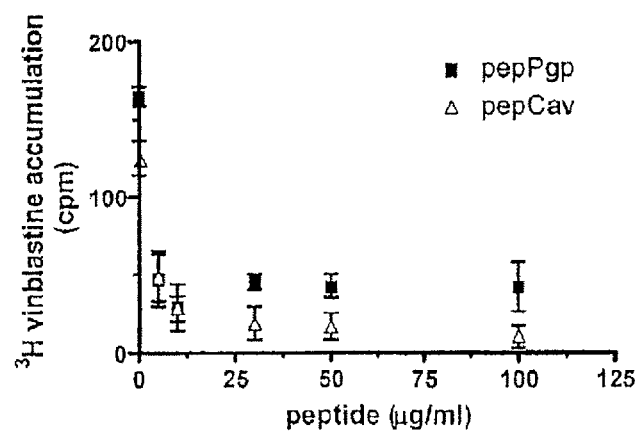

The effect of compounds PepPgp and PepCav on P-gp efflux transport activity was studied in Madin-Darby canine kidney (MDCK) cells stably transfected with MDR1. Cells were incubated in the presence of pepPgp or pepCav compounds (20 µg/ml). At different times following treatment, the accumulation of vinblastine, a specific substrate of P-gp, was measured. FIG. 1A shows that accumulation of [$^3$H]-vinblastine decreased as a function of time in the presence of both compounds. This result indicates that P-gp transport activity is stimulated in MDCK-MDR1 cells. Furthermore, the addition of increasing concentrations of compounds reduced [$^3$H]-vinblastine accumulation in MDCK-MDR1 cells (FIG. 1B). These results indicate that both exemplary compounds stimulate P-gp transport in a dose-dependent manner. These are the first results describing the action of stimulatory compounds on P-gp transport activity.

Example 2

Stimulation of the P-gp Efflux Transport Activity of Beta-Amyloid in Vitro

The effect of compounds on P-gp uptake of beta-amyloid is studied in MDCK cells. Cells are incubated with beta-amyloid (catalog number PRO-447 from ProSpec-Tany TechnoGene LTD), a specific substrate of P-gp. PepPgp or pepCav compounds (20 µg/ml) is then added. At different times of treatment, the accumulation of beta-amyloid is measured. A decrease in beta-amyloid uptake observed in the presence of either one of the compounds is indicative of their stimulatory effect on P-gp efflux transport activity.

Example 3

Stimulation of the P-gp Efflux Transport Activity in Vivo

Figure 2:
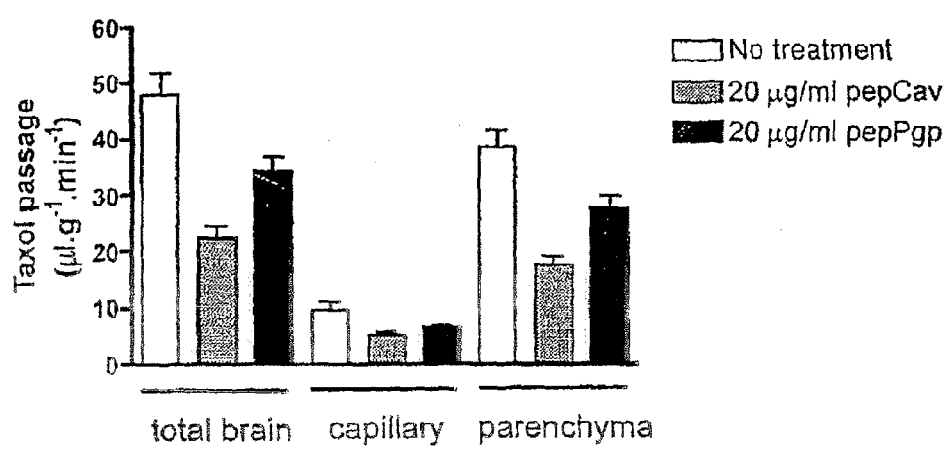
FIG. 2 is a graph showing decrease of TAXOL entering the brain upon treatment either with pepCav or with pepPgp.

The effect of compounds on P-gp efflux transport activity was investigated in vivo. For this purpose, the brain uptake of [$^3$H]-Taxol, a specific substrate of P-gp, was measured. [$^3$H]-Taxol was perfused into the brain through the right jugular vein for 5 minutes in the presence or absence of pepCav or pepPgp at a concentration of 20 µg/ml. Radioactivity of [$^3$H]-Taxol was analyzed in the total brain, the capillary and the parenchyma. As shown in FIG. 2, Taxol passage was reduced in the total brain by 50% and 30%, respectively, for pepCav and pepPgp as compared to control mice. The reduction was similar in the capillaries and in the parenchyma, indicating that the increased activity of P-gp reduced the accumulation of [$^3$H]-Taxol in endothelial cells as well as the brain uptake. These results indicate that the compounds are able to stimulate P-gp transport activity in vivo at the blood brain barrier.

Example 4

Inhibition of Cellular Migration

Figure 3A:
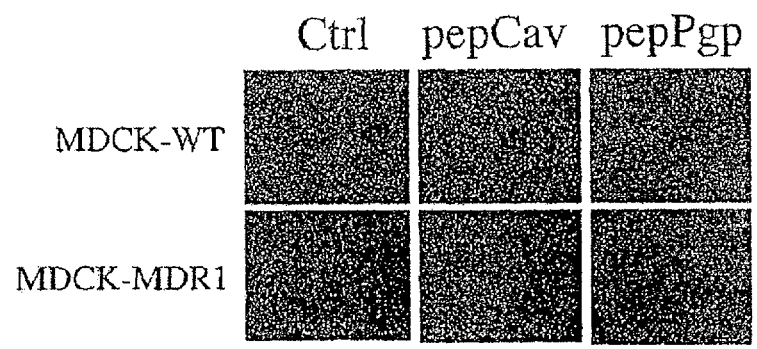
FIG. 3A is a set of photomicrographs showing decreased cellular migration upon administration of pepCav or pepPgp to cells.
Figure 3B:
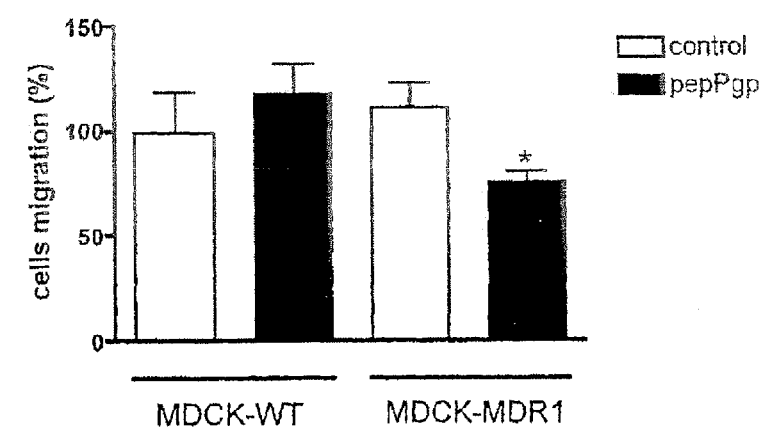
FIG. 3B is a pair of graphs showing decreased migration of MDCK cells that overexpress MDR1 upon administration of pepPgp or pepCav.
Figure 3B:
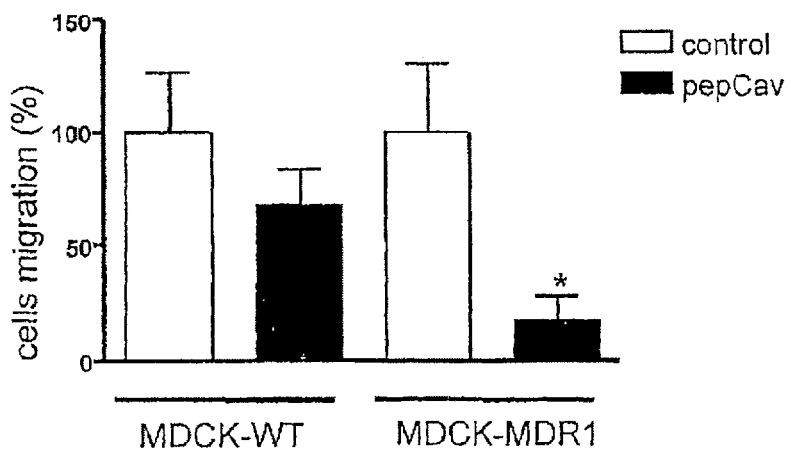

The effect of both compounds on cell migration, was determined by the migration of MDCK-MDR1 cells using Transwell filters (Costar; 8 µm pore size) precoated with 0.15% gelatin. Briefly, 1×10$^5$ cells were resuspended in 100 µl of serum-free medium with or without compounds (20 µg/ml). The lower chamber of the Transwell contained 10% serum used as chemoattractant. Cell migration was determined using a Nikon TMS-F microscope and Northern Eclipse Software. As observed in FIGS. 3A and 3B, pepPgp and pepCav inhibited cells migration of MDCK-MDR1 by 30% and 80%, respectively, as compared to the control.

Example 5

Inhibition of Angiogenesis in Vitro

Figure 4A:
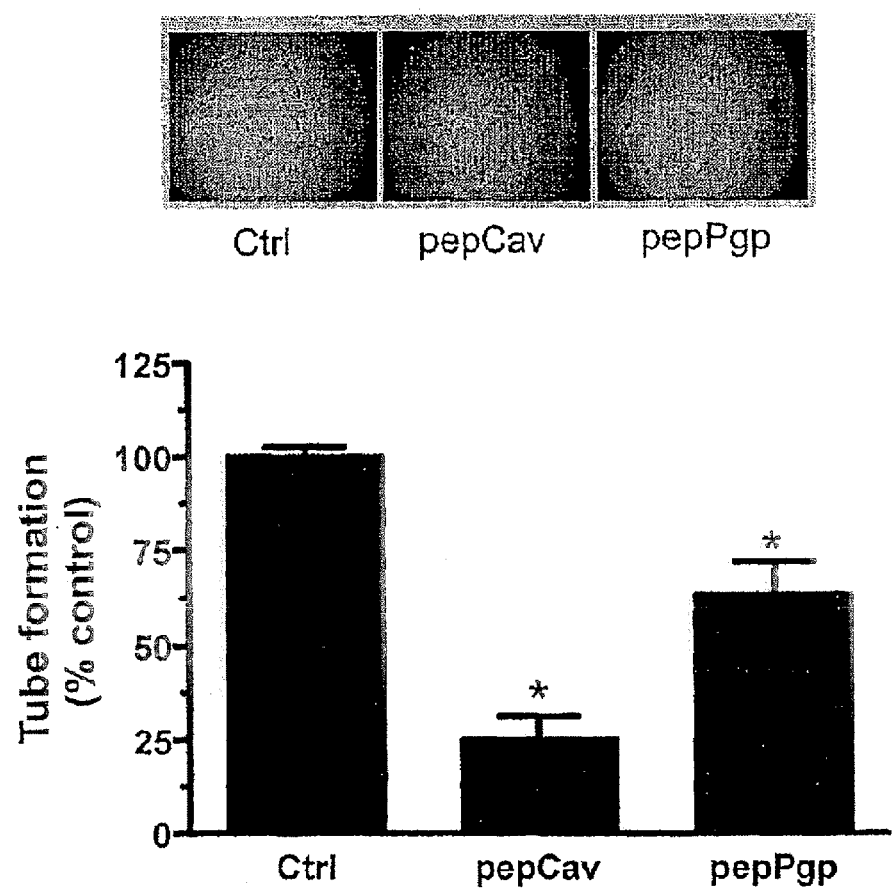
FIG. 4A is a photomicrograph and graph showing decreased tube (capillary) formation upon administration pepCav and pepPgp to HUVEC cells. This administration reduced the capillary-like structure formation by 75% and 40%, respectively.

The effect of these compounds on angiogenesis was evaluated in vitro using human umbilical vein endothelial cells (HUVEC) tube formation on Matrigel. Following transfections, cells were trypsinized and 2.5×10$^4$ cells were seeded on Matrigel. After cellular adhesion, the medium was removed and 100 µl fresh medium was added with or without 40 µg/ml of either pepCav or pepPgp. Tube formation was evaluated after 18 hours. After incubation, tubular structures were visualized at 60× magnification using a Nikon TMS-F microscope and Northern Eclipse Software. As shown in FIG. 4A, treatment of HUVEC cells with pepCav and pepPgp reduced the capillary-like structure formation by 75% and 40%, respectively.

Example 6

Inhibition of Angiogenesis in Vivo

Figure 4B:
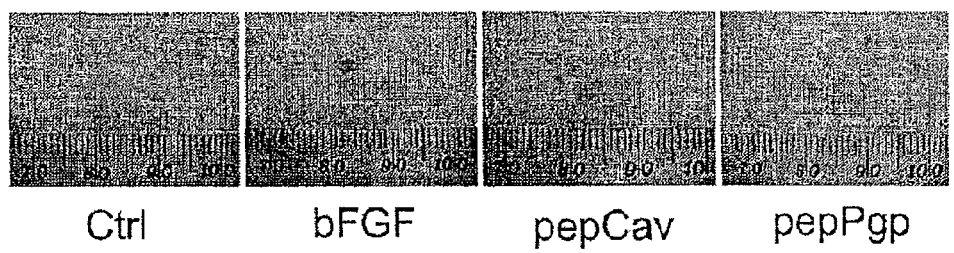
FIG. 4B is a photomicrograph and a graph showing decreased tube using the Matrigel plug assay. The graph shows measured hemoglobin content in the plug, a measure of capillary formation. PepCav and PepPgp reduced hemoglobin content by 25% and 40%, respectively as compared to the controls (bFGF alone).
Figure 4B:
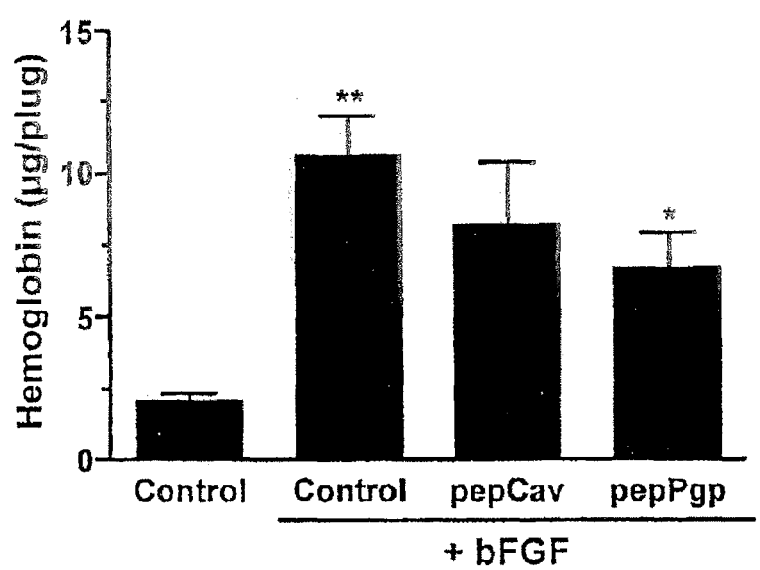

The effect of these compounds on angiogenesis was evaluated in vivo using the Matrigel plug assay. Briefly, Matrigel containing heparin and bFGF was injected under the skin of mice in the presence or absence of 100 µg/ml pepCav and pepPgp. The Matrigel plug was removed after one week. Hemoglobin content in the Matrigel plugs, which corresponds to the vessels formed, was measured. As indicated in FIG. 4B, treatment with 40 µg/ml pepCav and pepPgp reduced the hemoglobin content by 25% and 40%, respectively, indicating the both compounds inhibit angiogenesis in vivo.

Other Embodiments

All patents, patent applications including U.S. Provisional Application No. 60/852,678, filed Oct. 19, 2006, and publications mentioned in this specification are herein incorporated by reference to the same extent as if each independent patent, patent application, or publication was specifically and individually indicated to be incorporated by reference.

What is claimed is:

1. A soluble polypeptide comprising the amino acid sequence VFSMFRYSNWLDK (SEQ ID NO: 3), wherein said polypeptide
   is less than 1000 amino acids in length and
   specifically binds caveolin-1.

2. The polypeptide of claim 1 consisting of the amino acid sequence VFSMFRYSNWLDK (SEQ ID NO:3).

3. A method of increasing P-gp-mediated efflux in a cell, said method comprising administering a polypeptide of claim 1 in an amount sufficient to increase P-gp-mediated efflux.

4. A fusion protein comprising:

(a) a soluble polypeptide comprising the amino acid sequence VFSMFRYSNWLDK (SEQ ID NO:3), wherein said polypeptide is less than 1000 amino acids in length and specifically binds caveolin-1, and (b) a heterologous sequence.

* * * * *

UNITED STATES PATENT AND TRADEMARK OFFICE
CERTIFICATE OF CORRECTION

PATENT NO. : 8,487,072 B2
APPLICATION NO. : 12/446434
DATED : July 16, 2013
INVENTOR(S) : Richard Beliveau et al.

Page 1 of 1

It is certified that error appears in the above-identified patent and that said Letters Patent is hereby corrected as shown below:

On Title Page 1, References cited under OTHER PUBLICATIONS, in Kesari et al., replace "300-308)." with --300-308.--.

In the Specification

Column 8, TABLE 1, SEQ ID NO: 27, under fragment, replace "DGIWIKASFTTFT" with --DGIWKASFTTFT--.

Column 11, Line 48, replace "preprotyrypsin" with --preprotrypsin--;

Line 56, replace "1 to 13, 1 to 14, 1 to 15, 1 to 16, 1 to 17, 1 18," with --1 to 13, 1 to 14, 1 to 15, 1 to 16, 1 to 17, 1 to 18,--.

Column 15, Line 34, replace "charged (basic) amino acids include, arginine, lysine and" with --charged (basic) amino acids include arginine, lysine and--;

Line 35, replace "histidine. The nonpolar (hydrophobic) amino acids include," with --histidine. The nonpolar (hydrophobic) amino acids include--.

Column 21, Line 62, replace "polygalactin," with --polyglactin,--.

Signed and Sealed this
Twenty-fourth Day of February, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,487,072 B2 | Page 1 of 1 |
| APPLICATION NO. | : 12/446434 | |
| DATED | : July 16, 2013 | |
| INVENTOR(S) | : Beliveau et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 695 days.

Signed and Sealed this
Fifth Day of May, 2015

Michelle K. Lee
*Director of the United States Patent and Trademark Office*

```
                        SEQUENCE LISTING

<160> NUMBER OF SEQ ID NOS: 215

<210> SEQ ID NO 1
<211> LENGTH: 20
<212> TYPE: PRT
<213> ORGANISM: Artificial Sequence
<220> FEATURE:
<223> OTHER INFORMATION: synthetic

<400> SEQUENCE: 1

Asp Gly Ile Trp Lys Ala Ser Phe Thr Thr Phe Thr Val Thr Lys Tyr
1               5                   10                  15

Trp Phe Tyr Arg
            20

<210> SEQ ID NO 2
<211> LENGTH: 8
<212> TYPE: PRT
<213> ORGANISM: Artificial Sequence
<220> FEATURE:
<223> OTHER INFORMATION: synthetic

<400> SEQUENCE: 2

Val Thr Lys Tyr Trp Phe Tyr Arg
1               5

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Val Phe Ser Met Phe Arg Tyr Ser Asn Trp Leu Asp Lys
1               5                   10

<210> SEQ ID NO 4
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Phenylalanine, Tyrosine, or Tryptophan
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa = Phenylalanine, Tyrosine, or Tryptophan
<220> FEATURE:
<221> NAME/KEY: misc_feature
<222> LOCATION: (4)..(7)
<223> OTHER INFORMATION: Xaa can be any naturally occurring amino acid
```

```
<220> FEATURE:
<221> NAME/KEY: MISC_FEATURE
<222> LOCATION: (8)..(8)
<223> OTHER INFORMATION: Xaa = Phenylalanine, Tyrosine, or Tryptophan

<400> SEQUENCE: 4

Xaa Xaa Xaa Xaa Xaa Xaa Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Phenylalanine, Tyrosine, or Tryptophan
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Phenylalanine, Tyrosine, or Tryptophan
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa = Phenylalanine, Tyrosine, or Tryptophan

<400> SEQUENCE: 5

Xaa Xaa Xaa Xaa Xaa Xaa Xaa Xaa Xaa
1               5

<210> SEQ ID NO 6
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Phenylalanine, Tyrosine, or Tryptophan
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa = Phenylalanine, Tyrosine, or Tryptophan
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa = Phenylalanine, Tyrosine, or Tryptophan
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa = Phenylalanine, Tyrosine, or Tryptophan

<400> SEQUENCE: 6
```

```
Xaa Xaa Xaa Xaa Xaa Xaa Xaa Xaa Xaa Xaa Xaa
1               5                   10
```

```
<210> SEQ ID NO 7
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Leucine or Valine
<220> FEATURE:
<221> NAME/KEY: MISC_FEATURE
<222> LOCATION: (2)..(6)
<223> OTHER INFORMATION: Xaa = any amino acid or is missing
<220> FEATURE:
<221> NAME/KEY: MISC_FEATURE
<222> LOCATION: (8)..(12)
<223> OTHER INFORMATION: Xaa = any amino acid or is missing
<220> FEATURE:
<221> NAME/KEY: MISC_FEATURE
<222> LOCATION: (13)..(13)
<223> OTHER INFORMATION: Xaa = Lysine or Arginine

<400> SEQUENCE: 7

Xaa Xaa Xaa Xaa Xaa Xaa Tyr Xaa Xaa Xaa Xaa Xaa Xaa
1               5                   10
```

```
<210> SEQ ID NO 8
<211> LENGTH: 51
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(19)
<223> OTHER INFORMATION: Xaa is any amino acid or is missing
<220> FEATURE:
<221> NAME/KEY: MISC_FEATURE
<222> LOCATION: (20)..(20)
<223> OTHER INFORMATION: Xaa = Leu or Val
<220> FEATURE:
<221> NAME/KEY: MISC_FEATURE
<222> LOCATION: (21)..(25)
<223> OTHER INFORMATION: Xaa is any amino acid or is missing
<220> FEATURE:
<221> NAME/KEY: MISC_FEATURE
<222> LOCATION: (27)..(31)
<223> OTHER INFORMATION: Xaa is any amino acid or is missing
<220> FEATURE:
<221> NAME/KEY: MISC_FEATURE
<222> LOCATION: (32)..(32)
<223> OTHER INFORMATION: Xaa = Lys or Arg
<220> FEATURE:
<221> NAME/KEY: MISC_FEATURE
<222> LOCATION: (33)..(51)
<223> OTHER INFORMATION: Xaa is any amino acid or is missing

<400> SEQUENCE: 8

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Tyr Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa
    50
```

```
<210> SEQ ID NO 9
<211> LENGTH: 12
<212> TYPE: PRT
<213> ORGANISM: Artificial Sequence
<220> FEATURE:
<223> OTHER INFORMATION: synthetic

<400> SEQUENCE: 9

Ala Ser Phe Thr Thr Phe Thr Val Thr Lys Tyr Trp
1               5                   10

<210> SEQ ID NO 10
<211> LENGTH: 6
<212> TYPE: PRT
<213> ORGANISM: Artificial Sequence
<220> FEATURE:
<223> OTHER INFORMATION: synthetic

<400> SEQUENCE: 10

Trp Lys Ala Ser Phe Thr
1               5

<210> SEQ ID NO 11
<211> LENGTH: 19
<212> TYPE: PRT
<213> ORGANISM: Artificial Sequence
<220> FEATURE:
<223> OTHER INFORMATION: synthetic

<400> SEQUENCE: 11

Gly Ile Trp Lys Ala Ser Phe Thr Thr Phe Thr Val Thr Lys Tyr Trp
1               5                   10                  15

Phe Tyr Arg

<210> SEQ ID NO 12
<211> LENGTH: 12
<212> TYPE: PRT
<213> ORGANISM: Artificial Sequence
<220> FEATURE:
<223> OTHER INFORMATION: synthetic

<400> SEQUENCE: 12

Lys Ala Ser Phe Thr Thr Phe Thr Val Thr Lys Tyr
1               5                   10

<210> SEQ ID NO 13
<211> LENGTH: 8
<212> TYPE: PRT
<213> ORGANISM: Artificial Sequence
<220> FEATURE:
<223> OTHER INFORMATION: synthetic

<400> SEQUENCE: 13

Thr Val Thr Lys Tyr Trp Phe Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic

<400> SEQUENCE: 14

Ile Trp Lys Ala Ser Phe
1               5
```

```
<210> SEQ ID NO 15
<211> LENGTH: 19
<212> TYPE: PRT
<213> ORGANISM: Artificial Sequence
<220> FEATURE:
<223> OTHER INFORMATION: synthetic

<400> SEQUENCE: 15

Asp Gly Ile Trp Lys Ala Ser Phe Thr Thr Phe Thr Val Thr Lys Tyr
1               5                   10                  15

Trp Phe Tyr

<210> SEQ ID NO 16
<211> LENGTH: 12
<212> TYPE: PRT
<213> ORGANISM: Artificial Sequence
<220> FEATURE:
<223> OTHER INFORMATION: synthetic

<400> SEQUENCE: 16

Trp Lys Ala Ser Phe Thr Thr Phe Thr Val Thr Lys
1               5                   10

<210> SEQ ID NO 17
<211> LENGTH: 8
<212> TYPE: PRT
<213> ORGANISM: Artificial Sequence
<220> FEATURE:
<223> OTHER INFORMATION: synthetic

<400> SEQUENCE: 17

Phe Thr Val Thr Lys Tyr Trp Phe
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic

<400> SEQUENCE: 18

Gly Ile Trp Lys Ala Ser
1               5

<210> SEQ ID NO 19
<211> LENGTH: 18
<212> TYPE: PRT
<213> ORGANISM: Artificial Sequence
<220> FEATURE:
<223> OTHER INFORMATION: synthetic

<400> SEQUENCE: 19

Ile Trp Lys Ala Ser Phe Thr Thr Phe Thr Val Thr Lys Tyr Trp Phe
1               5                   10                  15

Tyr Arg

<210> SEQ ID NO 20
<211> LENGTH: 12
<212> TYPE: PRT
<213> ORGANISM: Artificial Sequence
<220> FEATURE:
<223> OTHER INFORMATION: synthetic

<400> SEQUENCE: 20

Ile Trp Lys Ala Ser Phe Thr Thr Phe Thr Val Thr
1               5                   10
```

```
<210> SEQ ID NO 21
<211> LENGTH: 8
<212> TYPE: PRT
<213> ORGANISM: Artificial Sequence
<220> FEATURE:
<223> OTHER INFORMATION: synthetic

<400> SEQUENCE: 21

Thr Phe Thr Val Thr Lys Tyr Trp
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic

<400> SEQUENCE: 22

Asp Gly Ile Trp Lys Ala
1               5

<210> SEQ ID NO 23
<211> LENGTH: 18
<212> TYPE: PRT
<213> ORGANISM: Artificial Sequence
<220> FEATURE:
<223> OTHER INFORMATION: synthetic

<400> SEQUENCE: 23

Gly Ile Trp Lys Ala Ser Phe Thr Thr Phe Thr Val Thr Lys Tyr Trp
1               5                   10                  15

Phe Tyr

<210> SEQ ID NO 24
<211> LENGTH: 12
<212> TYPE: PRT
<213> ORGANISM: Artificial Sequence
<220> FEATURE:
<223> OTHER INFORMATION: synthetic

<400> SEQUENCE: 24

Gly Ile Trp Lys Ala Ser Phe Thr Thr Phe Thr Val
1               5                   10

<210> SEQ ID NO 25
<211> LENGTH: 8
<212> TYPE: PRT
<213> ORGANISM: Artificial Sequence
<220> FEATURE:
<223> OTHER INFORMATION: synthetic

<400> SEQUENCE: 25

Thr Thr Phe Thr Val Thr Lys Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: synthetic

<400> SEQUENCE: 26

Tyr Trp Phe Tyr Arg
1               5
```

<210> SEQ ID NO 27
<211> LENGTH: 18
<212> TYPE: PRT
<213> ORGANISM: Artificial Sequence
<220> FEATURE:
<223> OTHER INFORMATION: synthetic

<400> SEQUENCE: 27

Asp Gly Ile Trp Lys Ala Ser Phe Thr Thr Phe Thr Val Thr Lys Tyr
1               5                   10                  15

Trp Phe

<210> SEQ ID NO 28
<211> LENGTH: 12
<212> TYPE: PRT
<213> ORGANISM: Artificial Sequence
<220> FEATURE:
<223> OTHER INFORMATION: synthetic

<400> SEQUENCE: 28

Asp Gly Ile Trp Lys Ala Ser Phe Thr Thr Phe Thr
1               5                   10

<210> SEQ ID NO 29
<211> LENGTH: 8
<212> TYPE: PRT
<213> ORGANISM: Artificial Sequence
<220> FEATURE:
<223> OTHER INFORMATION: synthetic

<400> SEQUENCE: 29

Phe Thr Thr Phe Thr Val Thr Lys
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic

<400> SEQUENCE: 30

Lys Tyr Trp Phe Tyr
1               5

<210> SEQ ID NO 31
<211> LENGTH: 17
<212> TYPE: PRT
<213> ORGANISM: Artificial Sequence
<220> FEATURE:
<223> OTHER INFORMATION: synthetic

<400> SEQUENCE: 31

Trp Lys Ala Ser Phe Thr Thr Phe Thr Val Thr Lys Tyr Trp Phe Tyr
1               5                   10                  15

Arg

<210> SEQ ID NO 32
<211> LENGTH: 11
<212> TYPE: PRT
<213> ORGANISM: Artificial Sequence
<220> FEATURE:
<223> OTHER INFORMATION: synthetic

<400> SEQUENCE: 32

```
Thr Phe Thr Val Thr Lys Tyr Trp Phe Tyr Arg
1               5                   10
```

<210> SEQ ID NO 33
<211> LENGTH: 8
<212> TYPE: PRT
<213> ORGANISM: Artificial Sequence
<220> FEATURE:
<223> OTHER INFORMATION: synthetic

<400> SEQUENCE: 33

```
Ser Phe Thr Thr Phe Thr Val Thr
1               5
```

<210> SEQ ID NO 34
<211> LENGTH: 5
<212> TYPE: PRT
<213> ORGANISM: Artificial Sequence
<220> FEATURE:
<223> OTHER INFORMATION: synthetic

<400> SEQUENCE: 34

```
Thr Lys Tyr Trp Phe
1               5
```

<210> SEQ ID NO 35
<211> LENGTH: 17
<212> TYPE: PRT
<213> ORGANISM: Artificial Sequence
<220> FEATURE:
<223> OTHER INFORMATION: synthetic

<400> SEQUENCE: 35

```
Ile Trp Lys Ala Ser Phe Thr Thr Phe Thr Val Thr Lys Tyr Trp Phe
1               5                   10                  15
Tyr
```

<210> SEQ ID NO 36
<211> LENGTH: 11
<212> TYPE: PRT
<213> ORGANISM: Artificial Sequence
<220> FEATURE:
<223> OTHER INFORMATION: synthetic

<400> SEQUENCE: 36

```
Thr Thr Phe Thr Val Thr Lys Tyr Trp Phe Tyr
1               5                   10
```

<210> SEQ ID NO 37
<211> LENGTH: 8
<212> TYPE: PRT
<213> ORGANISM: Artificial Sequence
<220> FEATURE:
<223> OTHER INFORMATION: synthetic

<400> SEQUENCE: 37

```
Ala Ser Phe Thr Thr Phe Thr Val
1               5
```

<210> SEQ ID NO 38
<211> LENGTH: 5
<212> TYPE: PRT
<213> ORGANISM: Artificial Sequence
<220> FEATURE:
<223> OTHER INFORMATION: synthetic

<400> SEQUENCE: 38

```
Val Thr Lys Tyr Trp
1               5

<210> SEQ ID NO 39
<211> LENGTH: 17
<212> TYPE: PRT
<213> ORGANISM: Artificial Sequence
<220> FEATURE:
<223> OTHER INFORMATION: synthetic

<400> SEQUENCE: 39

Gly Ile Trp Lys Ala Ser Phe Thr Thr Phe Thr Val Thr Lys Tyr Trp
1               5                   10                  15

Phe

<210> SEQ ID NO 40
<211> LENGTH: 11
<212> TYPE: PRT
<213> ORGANISM: Artificial Sequence
<220> FEATURE:
<223> OTHER INFORMATION: synthetic

<400> SEQUENCE: 40

Phe Thr Thr Phe Thr Val Thr Lys Tyr Trp Phe
1               5                   10

<210> SEQ ID NO 41
<211> LENGTH: 8
<212> TYPE: PRT
<213> ORGANISM: Artificial Sequence
<220> FEATURE:
<223> OTHER INFORMATION: synthetic

<400> SEQUENCE: 41

Lys Ala Ser Phe Thr Thr Phe Thr
1               5

<210> SEQ ID NO 42
<211> LENGTH: 5
<212> TYPE: PRT
<213> ORGANISM: Artificial Sequence
<220> FEATURE:
<223> OTHER INFORMATION: synthetic

<400> SEQUENCE: 42

Thr Val Thr Lys Tyr
1               5

<210> SEQ ID NO 43
<211> LENGTH: 17
<212> TYPE: PRT
<213> ORGANISM: Artificial Sequence
<220> FEATURE:
<223> OTHER INFORMATION: synthetic

<400> SEQUENCE: 43

Asp Gly Ile Trp Lys Ala Ser Phe Thr Thr Phe Thr Val Thr Lys Tyr
1               5                   10                  15

Trp

<210> SEQ ID NO 44
<211> LENGTH: 11
<212> TYPE: PRT
<213> ORGANISM: Artificial Sequence
<220> FEATURE:
<223> OTHER INFORMATION: synthetic
```

```
<400> SEQUENCE: 44

Ser Phe Thr Thr Phe Thr Val Thr Lys Tyr Trp
1               5                   10

<210> SEQ ID NO 45
<211> LENGTH: 8
<212> TYPE: PRT
<213> ORGANISM: Artificial Sequence
<220> FEATURE:
<223> OTHER INFORMATION: synthetic

<400> SEQUENCE: 45

Trp Lys Ala Ser Phe Thr Thr Phe
1               5

<210> SEQ ID NO 46
<211> LENGTH: 5
<212> TYPE: PRT
<213> ORGANISM: Artificial Sequence
<220> FEATURE:
<223> OTHER INFORMATION: synthetic

<400> SEQUENCE: 46

Phe Thr Val Thr Lys
1               5

<210> SEQ ID NO 47
<211> LENGTH: 16
<212> TYPE: PRT
<213> ORGANISM: Artificial Sequence
<220> FEATURE:
<223> OTHER INFORMATION: synthetic

<400> SEQUENCE: 47

Lys Ala Ser Phe Thr Thr Phe Thr Val Thr Lys Tyr Trp Phe Tyr Arg
1               5                   10                  15

<210> SEQ ID NO 48
<211> LENGTH: 11
<212> TYPE: PRT
<213> ORGANISM: Artificial Sequence
<220> FEATURE:
<223> OTHER INFORMATION: synthetic

<400> SEQUENCE: 48

Ala Ser Phe Thr Thr Phe Thr Val Thr Lys Tyr
1               5                   10

<210> SEQ ID NO 49
<211> LENGTH: 8
<212> TYPE: PRT
<213> ORGANISM: Artificial Sequence
<220> FEATURE:
<223> OTHER INFORMATION: synthetic

<400> SEQUENCE: 49

Ile Trp Lys Ala Ser Phe Thr Thr
1               5

<210> SEQ ID NO 50
<211> LENGTH: 5
<212> TYPE: PRT
<213> ORGANISM: Artificial Sequence
<220> FEATURE:
<223> OTHER INFORMATION: synthetic

<400> SEQUENCE: 50
```

```
Thr Phe Thr Val Thr
1               5

<210> SEQ ID NO 51
<211> LENGTH: 16
<212> TYPE: PRT
<213> ORGANISM: Artificial Sequence
<220> FEATURE:
<223> OTHER INFORMATION: synthetic

<400> SEQUENCE: 51

Trp Lys Ala Ser Phe Thr Thr Phe Thr Val Thr Lys Tyr Trp Phe Tyr
1               5                   10                  15

<210> SEQ ID NO 52
<211> LENGTH: 11
<212> TYPE: PRT
<213> ORGANISM: Artificial Sequence
<220> FEATURE:
<223> OTHER INFORMATION: synthetic

<400> SEQUENCE: 52

Lys Ala Ser Phe Thr Thr Phe Thr Val Thr Lys
1               5                   10

<210> SEQ ID NO 53
<211> LENGTH: 8
<212> TYPE: PRT
<213> ORGANISM: Artificial Sequence
<220> FEATURE:
<223> OTHER INFORMATION: synthetic

<400> SEQUENCE: 53

Gly Ile Trp Lys Ala Ser Phe Thr
1               5

<210> SEQ ID NO 54
<211> LENGTH: 5
<212> TYPE: PRT
<213> ORGANISM: Artificial Sequence
<220> FEATURE:
<223> OTHER INFORMATION: synthetic

<400> SEQUENCE: 54

Thr Thr Phe Thr Val
1               5

<210> SEQ ID NO 55
<211> LENGTH: 16
<212> TYPE: PRT
<213> ORGANISM: Artificial Sequence
<220> FEATURE:
<223> OTHER INFORMATION: synthetic

<400> SEQUENCE: 55

Ile Trp Lys Ala Ser Phe Thr Thr Phe Thr Val Thr Lys Tyr Trp Phe
1               5                   10                  15

<210> SEQ ID NO 56
<211> LENGTH: 11
<212> TYPE: PRT
<213> ORGANISM: Artificial Sequence
<220> FEATURE:
<223> OTHER INFORMATION: synthetic

<400> SEQUENCE: 56

Trp Lys Ala Ser Phe Thr Thr Phe Thr Val Thr
1               5                   10
```

```
<210> SEQ ID NO 57
<211> LENGTH: 8
<212> TYPE: PRT
<213> ORGANISM: Artificial Sequence
<220> FEATURE:
<223> OTHER INFORMATION: synthetic

<400> SEQUENCE: 57

Asp Gly Ile Trp Lys Ala Ser Phe
1               5

<210> SEQ ID NO 58
<211> LENGTH: 5
<212> TYPE: PRT
<213> ORGANISM: Artificial Sequence
<220> FEATURE:
<223> OTHER INFORMATION: synthetic

<400> SEQUENCE: 58

Phe Thr Thr Phe Thr
1               5

<210> SEQ ID NO 59
<211> LENGTH: 16
<212> TYPE: PRT
<213> ORGANISM: Artificial Sequence
<220> FEATURE:
<223> OTHER INFORMATION: synthetic

<400> SEQUENCE: 59

Gly Ile Trp Lys Ala Ser Phe Thr Thr Phe Thr Val Thr Lys Tyr Trp
1               5                   10                  15

<210> SEQ ID NO 60
<211> LENGTH: 11
<212> TYPE: PRT
<213> ORGANISM: Artificial Sequence
<220> FEATURE:
<223> OTHER INFORMATION: synthetic

<400> SEQUENCE: 60

Ile Trp Lys Ala Ser Phe Thr Thr Phe Thr Val
1               5                   10

<210> SEQ ID NO 61
<211> LENGTH: 7
<212> TYPE: PRT
<213> ORGANISM: Artificial Sequence
<220> FEATURE:
<223> OTHER INFORMATION: synthetic

<400> SEQUENCE: 61

Thr Lys Tyr Trp Phe Tyr Arg
1               5

<210> SEQ ID NO 62
<211> LENGTH: 5
<212> TYPE: PRT
<213> ORGANISM: Artificial Sequence
<220> FEATURE:
<223> OTHER INFORMATION: synthetic

<400> SEQUENCE: 62

Ser Phe Thr Thr Phe
1               5
```

```
<210> SEQ ID NO 63
<211> LENGTH: 16
<212> TYPE: PRT
<213> ORGANISM: Artificial Sequence
<220> FEATURE:
<223> OTHER INFORMATION: synthetic

<400> SEQUENCE: 63

Asp Gly Ile Trp Lys Ala Ser Phe Thr Thr Phe Thr Val Thr Lys Tyr
1               5                   10                  15

<210> SEQ ID NO 64
<211> LENGTH: 11
<212> TYPE: PRT
<213> ORGANISM: Artificial Sequence
<220> FEATURE:
<223> OTHER INFORMATION: synthetic

<400> SEQUENCE: 64

Gly Ile Trp Lys Ala Ser Phe Thr Thr Phe Thr
1               5                   10

<210> SEQ ID NO 65
<211> LENGTH: 7
<212> TYPE: PRT
<213> ORGANISM: Artificial Sequence
<220> FEATURE:
<223> OTHER INFORMATION: synthetic

<400> SEQUENCE: 65

Val Thr Lys Tyr Trp Phe Tyr
1               5

<210> SEQ ID NO 66
<211> LENGTH: 5
<212> TYPE: PRT
<213> ORGANISM: Artificial Sequence
<220> FEATURE:
<223> OTHER INFORMATION: synthetic

<400> SEQUENCE: 66

Ala Ser Phe Thr Thr
1               5

<210> SEQ ID NO 67
<211> LENGTH: 15
<212> TYPE: PRT
<213> ORGANISM: Artificial Sequence
<220> FEATURE:
<223> OTHER INFORMATION: synthetic

<400> SEQUENCE: 67

Ala Ser Phe Thr Thr Phe Thr Val Thr Lys Tyr Trp Phe Tyr Arg
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: synthetic

<400> SEQUENCE: 68

Asp Gly Ile Trp Lys Ala Ser Phe Thr Thr Phe
1               5                   10

<210> SEQ ID NO 69
<211> LENGTH: 7
```

```
<212> TYPE: PRT
<213> ORGANISM: Artificial Sequence
<220> FEATURE:
<223> OTHER INFORMATION: synthetic

<400> SEQUENCE: 69

Thr Val Thr Lys Tyr Trp Phe
1               5

<210> SEQ ID NO 70
<211> LENGTH: 5
<212> TYPE: PRT
<213> ORGANISM: Artificial Sequence
<220> FEATURE:
<223> OTHER INFORMATION: synthetic

<400> SEQUENCE: 70

Lys Ala Ser Phe Thr
1               5

<210> SEQ ID NO 71
<211> LENGTH: 15
<212> TYPE: PRT
<213> ORGANISM: Artificial Sequence
<220> FEATURE:
<223> OTHER INFORMATION: synthetic

<400> SEQUENCE: 71

Lys Ala Ser Phe Thr Thr Phe Thr Val Thr Lys Tyr Trp Phe Tyr
1               5                   10                  15

<210> SEQ ID NO 72
<211> LENGTH: 10
<212> TYPE: PRT
<213> ORGANISM: Artificial Sequence
<220> FEATURE:
<223> OTHER INFORMATION: synthetic

<400> SEQUENCE: 72

Phe Thr Val Thr Lys Tyr Trp Phe Tyr Arg
1               5                   10

<210> SEQ ID NO 73
<211> LENGTH: 7
<212> TYPE: PRT
<213> ORGANISM: Artificial Sequence
<220> FEATURE:
<223> OTHER INFORMATION: synthetic

<400> SEQUENCE: 73

Phe Thr Val Thr Lys Tyr Trp
1               5

<210> SEQ ID NO 74
<211> LENGTH: 5
<212> TYPE: PRT
<213> ORGANISM: Artificial Sequence
<220> FEATURE:
<223> OTHER INFORMATION: synthetic

<400> SEQUENCE: 74

Trp Lys Ala Ser Phe
1               5

<210> SEQ ID NO 75
<211> LENGTH: 15
<212> TYPE: PRT
<213> ORGANISM: Artificial Sequence
```

```
<220> FEATURE:
<223> OTHER INFORMATION: synthetic

<400> SEQUENCE: 75

Trp Lys Ala Ser Phe Thr Thr Phe Thr Val Thr Lys Tyr Trp Phe
1               5                   10                  15

<210> SEQ ID NO 76
<211> LENGTH: 10
<212> TYPE: PRT
<213> ORGANISM: Artificial Sequence
<220> FEATURE:
<223> OTHER INFORMATION: synthetic

<400> SEQUENCE: 76

Thr Phe Thr Val Thr Lys Tyr Trp Phe Tyr
1               5                   10

<210> SEQ ID NO 77
<211> LENGTH: 7
<212> TYPE: PRT
<213> ORGANISM: Artificial Sequence
<220> FEATURE:
<223> OTHER INFORMATION: synthetic

<400> SEQUENCE: 77

Thr Phe Thr Val Thr Lys Tyr
1               5

<210> SEQ ID NO 78
<211> LENGTH: 5
<212> TYPE: PRT
<213> ORGANISM: Artificial Sequence
<220> FEATURE:
<223> OTHER INFORMATION: synthetic

<400> SEQUENCE: 78

Ile Trp Lys Ala Ser
1               5

<210> SEQ ID NO 79
<211> LENGTH: 15
<212> TYPE: PRT
<213> ORGANISM: Artificial Sequence
<220> FEATURE:
<223> OTHER INFORMATION: synthetic

<400> SEQUENCE: 79

Ile Trp Lys Ala Ser Phe Thr Thr Phe Thr Val Thr Lys Tyr Trp
1               5                   10                  15

<210> SEQ ID NO 80
<211> LENGTH: 10
<212> TYPE: PRT
<213> ORGANISM: Artificial Sequence
<220> FEATURE:
<223> OTHER INFORMATION: synthetic

<400> SEQUENCE: 80

Thr Thr Phe Thr Val Thr Lys Tyr Trp Phe
1               5                   10

<210> SEQ ID NO 81
<211> LENGTH: 7
<212> TYPE: PRT
<213> ORGANISM: Artificial Sequence
<220> FEATURE:
<223> OTHER INFORMATION: synthetic
```

<400> SEQUENCE: 81

Thr Thr Phe Thr Val Thr Lys
1               5

<210> SEQ ID NO 82
<211> LENGTH: 5
<212> TYPE: PRT
<213> ORGANISM: Artificial Sequence
<220> FEATURE:
<223> OTHER INFORMATION: synthetic

<400> SEQUENCE: 82

Gly Ile Trp Lys Ala
1               5

<210> SEQ ID NO 83
<211> LENGTH: 15
<212> TYPE: PRT
<213> ORGANISM: Artificial Sequence
<220> FEATURE:
<223> OTHER INFORMATION: synthetic

<400> SEQUENCE: 83

Gly Ile Trp Lys Ala Ser Phe Thr Thr Phe Thr Val Thr Lys Tyr
1               5                   10                  15

<210> SEQ ID NO 84
<211> LENGTH: 10
<212> TYPE: PRT
<213> ORGANISM: Artificial Sequence
<220> FEATURE:
<223> OTHER INFORMATION: synthetic

<400> SEQUENCE: 84

Phe Thr Thr Phe Thr Val Thr Lys Tyr Trp
1               5                   10

<210> SEQ ID NO 85
<211> LENGTH: 7
<212> TYPE: PRT
<213> ORGANISM: Artificial Sequence
<220> FEATURE:
<223> OTHER INFORMATION: synthetic

<400> SEQUENCE: 85

Phe Thr Thr Phe Thr Val Thr
1               5

<210> SEQ ID NO 86
<211> LENGTH: 5
<212> TYPE: PRT
<213> ORGANISM: Artificial Sequence
<220> FEATURE:
<223> OTHER INFORMATION: synthetic

<400> SEQUENCE: 86

Asp Gly Ile Trp Lys
1               5

<210> SEQ ID NO 87
<211> LENGTH: 15
<212> TYPE: PRT
<213> ORGANISM: Artificial Sequence
<220> FEATURE:
<223> OTHER INFORMATION: synthetic

<400> SEQUENCE: 87

Asp Gly Ile Trp Lys Ala Ser Phe Thr Thr Phe Thr Val Thr Lys
1               5                   10                  15

<210> SEQ ID NO 88
<211> LENGTH: 10
<212> TYPE: PRT
<213> ORGANISM: Artificial Sequence
<220> FEATURE:
<223> OTHER INFORMATION: synthetic

<400> SEQUENCE: 88

Ser Phe Thr Thr Phe Thr Val Thr Lys Tyr
1               5                   10

<210> SEQ ID NO 89
<211> LENGTH: 7
<212> TYPE: PRT
<213> ORGANISM: Artificial Sequence
<220> FEATURE:
<223> OTHER INFORMATION: synthetic

<400> SEQUENCE: 89

Ser Phe Thr Thr Phe Thr Val
1               5

<210> SEQ ID NO 90
<211> LENGTH: 4
<212> TYPE: PRT
<213> ORGANISM: Artificial Sequence
<220> FEATURE:
<223> OTHER INFORMATION: synthetic

<400> SEQUENCE: 90

Trp Phe Tyr Arg
1

<210> SEQ ID NO 91
<211> LENGTH: 14
<212> TYPE: PRT
<213> ORGANISM: Artificial Sequence
<220> FEATURE:
<223> OTHER INFORMATION: synthetic

<400> SEQUENCE: 91

Ser Phe Thr Thr Phe Thr Val Thr Lys Tyr Trp Phe Tyr Arg
1               5                   10

<210> SEQ ID NO 92
<211> LENGTH: 10
<212> TYPE: PRT
<213> ORGANISM: Artificial Sequence
<220> FEATURE:
<223> OTHER INFORMATION: synthetic

<400> SEQUENCE: 92

Ala Ser Phe Thr Thr Phe Thr Val Thr Lys
1               5                   10

<210> SEQ ID NO 93
<211> LENGTH: 7
<212> TYPE: PRT
<213> ORGANISM: Artificial Sequence
<220> FEATURE:
<223> OTHER INFORMATION: synthetic

<400> SEQUENCE: 93

Ala Ser Phe Thr Thr Phe Thr

<210> SEQ ID NO 94
<211> LENGTH: 4
<212> TYPE: PRT
<213> ORGANISM: Artificial Sequence
<220> FEATURE:
<223> OTHER INFORMATION: synthetic

<400> SEQUENCE: 94

Tyr Trp Phe Tyr
1

<210> SEQ ID NO 95
<211> LENGTH: 14
<212> TYPE: PRT
<213> ORGANISM: Artificial Sequence
<220> FEATURE:
<223> OTHER INFORMATION: synthetic

<400> SEQUENCE: 95

Ala Ser Phe Thr Thr Phe Thr Val Thr Lys Tyr Trp Phe Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: synthetic

<400> SEQUENCE: 96

Lys Ala Ser Phe Thr Thr Phe Thr Val Thr
1               5                   10

<210> SEQ ID NO 97
<211> LENGTH: 7
<212> TYPE: PRT
<213> ORGANISM: Artificial Sequence
<220> FEATURE:
<223> OTHER INFORMATION: synthetic

<400> SEQUENCE: 97

Lys Ala Ser Phe Thr Thr Phe
1               5

<210> SEQ ID NO 98
<211> LENGTH: 4
<212> TYPE: PRT
<213> ORGANISM: Artificial Sequence
<220> FEATURE:
<223> OTHER INFORMATION: synthetic

<400> SEQUENCE: 98

Lys Tyr Trp Phe
1

<210> SEQ ID NO 99
<211> LENGTH: 14
<212> TYPE: PRT
<213> ORGANISM: Artificial Sequence
<220> FEATURE:
<223> OTHER INFORMATION: synthetic

<400> SEQUENCE: 99

Lys Ala Ser Phe Thr Thr Phe Thr Val Thr Lys Tyr Trp Phe
1               5                   10

<210> SEQ ID NO 100
<211> LENGTH: 10
<212> TYPE: PRT
<213> ORGANISM: Artificial Sequence
<220> FEATURE:
<223> OTHER INFORMATION: synthetic

<400> SEQUENCE: 100

Trp Lys Ala Ser Phe Thr Thr Phe Thr Val
1               5                   10

<210> SEQ ID NO 101
<211> LENGTH: 7
<212> TYPE: PRT
<213> ORGANISM: Artificial Sequence
<220> FEATURE:
<223> OTHER INFORMATION: synthetic

<400> SEQUENCE: 101

Trp Lys Ala Ser Phe Thr Thr
1               5

<210> SEQ ID NO 102
<211> LENGTH: 4
<212> TYPE: PRT
<213> ORGANISM: Artificial Sequence
<220> FEATURE:
<223> OTHER INFORMATION: synthetic

<400> SEQUENCE: 102

Thr Lys Tyr Trp
1

<210> SEQ ID NO 103
<211> LENGTH: 14
<212> TYPE: PRT
<213> ORGANISM: Artificial Sequence
<220> FEATURE:
<223> OTHER INFORMATION: synthetic

<400> SEQUENCE: 103

Trp Lys Ala Ser Phe Thr Thr Phe Thr Val Thr Lys Tyr Trp
1               5                   10

<210> SEQ ID NO 104
<211> LENGTH: 10
<212> TYPE: PRT
<213> ORGANISM: Artificial Sequence
<220> FEATURE:
<223> OTHER INFORMATION: synthetic

<400> SEQUENCE: 104

Ile Trp Lys Ala Ser Phe Thr Thr Phe Thr
1               5                   10

<210> SEQ ID NO 105
<211> LENGTH: 7
<212> TYPE: PRT
<213> ORGANISM: Artificial Sequence
<220> FEATURE:
<223> OTHER INFORMATION: synthetic

<400> SEQUENCE: 105

Ile Trp Lys Ala Ser Phe Thr
1               5

<210> SEQ ID NO 106

```
<211> LENGTH: 4
<212> TYPE: PRT
<213> ORGANISM: Artificial Sequence
<220> FEATURE:
<223> OTHER INFORMATION: synthetic

<400> SEQUENCE: 106

Val Thr Lys Tyr
1

<210> SEQ ID NO 107
<211> LENGTH: 14
<212> TYPE: PRT
<213> ORGANISM: Artificial Sequence
<220> FEATURE:
<223> OTHER INFORMATION: synthetic

<400> SEQUENCE: 107

Ile Trp Lys Ala Ser Phe Thr Thr Phe Thr Val Thr Lys Tyr
1               5                   10

<210> SEQ ID NO 108
<211> LENGTH: 10
<212> TYPE: PRT
<213> ORGANISM: Artificial Sequence
<220> FEATURE:
<223> OTHER INFORMATION: synthetic

<400> SEQUENCE: 108

Gly Ile Trp Lys Ala Ser Phe Thr Thr Phe
1               5                   10

<210> SEQ ID NO 109
<211> LENGTH: 7
<212> TYPE: PRT
<213> ORGANISM: Artificial Sequence
<220> FEATURE:
<223> OTHER INFORMATION: synthetic

<400> SEQUENCE: 109

Gly Ile Trp Lys Ala Ser Phe
1               5

<210> SEQ ID NO 110
<211> LENGTH: 4
<212> TYPE: PRT
<213> ORGANISM: Artificial Sequence
<220> FEATURE:
<223> OTHER INFORMATION: synthetic

<400> SEQUENCE: 110

Thr Val Thr Lys
1

<210> SEQ ID NO 111
<211> LENGTH: 14
<212> TYPE: PRT
<213> ORGANISM: Artificial Sequence
<220> FEATURE:
<223> OTHER INFORMATION: synthetic

<400> SEQUENCE: 111

Gly Ile Trp Lys Ala Ser Phe Thr Thr Phe Thr Val Thr Lys
1               5                   10

<210> SEQ ID NO 112
<211> LENGTH: 10
<212> TYPE: PRT
```

```
<213> ORGANISM: Artificial Sequence
<220> FEATURE:
<223> OTHER INFORMATION: synthetic

<400> SEQUENCE: 112

Asp Gly Ile Trp Lys Ala Ser Phe Thr Thr
1               5                   10

<210> SEQ ID NO 113
<211> LENGTH: 7
<212> TYPE: PRT
<213> ORGANISM: Artificial Sequence
<220> FEATURE:
<223> OTHER INFORMATION: synthetic

<400> SEQUENCE: 113

Asp Gly Ile Trp Lys Ala Ser
1               5

<210> SEQ ID NO 114
<211> LENGTH: 4
<212> TYPE: PRT
<213> ORGANISM: Artificial Sequence
<220> FEATURE:
<223> OTHER INFORMATION: synthetic

<400> SEQUENCE: 114

Phe Thr Val Thr
1

<210> SEQ ID NO 115
<211> LENGTH: 14
<212> TYPE: PRT
<213> ORGANISM: Artificial Sequence
<220> FEATURE:
<223> OTHER INFORMATION: synthetic

<400> SEQUENCE: 115

Asp Gly Ile Trp Lys Ala Ser Phe Thr Thr Phe Thr Val Thr
1               5                   10

<210> SEQ ID NO 116
<211> LENGTH: 9
<212> TYPE: PRT
<213> ORGANISM: Artificial Sequence
<220> FEATURE:
<223> OTHER INFORMATION: synthetic

<400> SEQUENCE: 116

Thr Val Thr Lys Tyr Trp Phe Tyr Arg
1               5

<210> SEQ ID NO 117
<211> LENGTH: 6
<212> TYPE: PRT
<213> ORGANISM: Artificial Sequence
<220> FEATURE:
<223> OTHER INFORMATION: synthetic

<400> SEQUENCE: 117

Lys Tyr Trp Phe Tyr Arg
1               5

<210> SEQ ID NO 118
<211> LENGTH: 4
<212> TYPE: PRT
<213> ORGANISM: Artificial Sequence
<220> FEATURE:
```

<223> OTHER INFORMATION: synthetic

<400> SEQUENCE: 118

Thr Phe Thr Val
1

<210> SEQ ID NO 119
<211> LENGTH: 13
<212> TYPE: PRT
<213> ORGANISM: Artificial Sequence
<220> FEATURE:
<223> OTHER INFORMATION: synthetic

<400> SEQUENCE: 119

Phe Thr Thr Phe Thr Val Thr Lys Tyr Trp Phe Tyr Arg
1               5                   10

<210> SEQ ID NO 120
<211> LENGTH: 9
<212> TYPE: PRT
<213> ORGANISM: Artificial Sequence
<220> FEATURE:
<223> OTHER INFORMATION: synthetic

<400> SEQUENCE: 120

Phe Thr Val Thr Lys Tyr Trp Phe Tyr
1               5

<210> SEQ ID NO 121
<211> LENGTH: 6
<212> TYPE: PRT
<213> ORGANISM: Artificial Sequence
<220> FEATURE:
<223> OTHER INFORMATION: synthetic

<400> SEQUENCE: 121

Thr Lys Tyr Trp Phe Tyr
1               5

<210> SEQ ID NO 122
<211> LENGTH: 4
<212> TYPE: PRT
<213> ORGANISM: Artificial Sequence
<220> FEATURE:
<223> OTHER INFORMATION: synthetic

<400> SEQUENCE: 122

Thr Thr Phe Thr
1

<210> SEQ ID NO 123
<211> LENGTH: 13
<212> TYPE: PRT
<213> ORGANISM: Artificial Sequence
<220> FEATURE:
<223> OTHER INFORMATION: synthetic

<400> SEQUENCE: 123

Ser Phe Thr Thr Phe Thr Val Thr Lys Tyr Trp Phe Tyr
1               5                   10

<210> SEQ ID NO 124
<211> LENGTH: 9
<212> TYPE: PRT
<213> ORGANISM: Artificial Sequence
<220> FEATURE:
<223> OTHER INFORMATION: synthetic

```
<400> SEQUENCE: 124

Thr Phe Thr Val Thr Lys Tyr Trp Phe
1               5

<210> SEQ ID NO 125
<211> LENGTH: 6
<212> TYPE: PRT
<213> ORGANISM: Artificial Sequence
<220> FEATURE:
<223> OTHER INFORMATION: synthetic

<400> SEQUENCE: 125

Val Thr Lys Tyr Trp Phe
1               5

<210> SEQ ID NO 126
<211> LENGTH: 4
<212> TYPE: PRT
<213> ORGANISM: Artificial Sequence
<220> FEATURE:
<223> OTHER INFORMATION: synthetic

<400> SEQUENCE: 126

Phe Thr Thr Phe
1

<210> SEQ ID NO 127
<211> LENGTH: 13
<212> TYPE: PRT
<213> ORGANISM: Artificial Sequence
<220> FEATURE:
<223> OTHER INFORMATION: synthetic

<400> SEQUENCE: 127

Ala Ser Phe Thr Thr Phe Thr Val Thr Lys Tyr Trp Phe
1               5                   10

<210> SEQ ID NO 128
<211> LENGTH: 9
<212> TYPE: PRT
<213> ORGANISM: Artificial Sequence
<220> FEATURE:
<223> OTHER INFORMATION: synthetic

<400> SEQUENCE: 128

Thr Thr Phe Thr Val Thr Lys Tyr Trp
1               5

<210> SEQ ID NO 129
<211> LENGTH: 6
<212> TYPE: PRT
<213> ORGANISM: Artificial Sequence
<220> FEATURE:
<223> OTHER INFORMATION: synthetic

<400> SEQUENCE: 129

Thr Val Thr Lys Tyr Trp
1               5

<210> SEQ ID NO 130
<211> LENGTH: 4
<212> TYPE: PRT
<213> ORGANISM: Artificial Sequence
<220> FEATURE:
<223> OTHER INFORMATION: synthetic

<400> SEQUENCE: 130
```

Ser Phe Thr Thr
1

<210> SEQ ID NO 131
<211> LENGTH: 13
<212> TYPE: PRT
<213> ORGANISM: Artificial Sequence
<220> FEATURE:
<223> OTHER INFORMATION: synthetic

<400> SEQUENCE: 131

Lys Ala Ser Phe Thr Thr Phe Thr Val Thr Lys Tyr Trp
1               5                   10

<210> SEQ ID NO 132
<211> LENGTH: 9
<212> TYPE: PRT
<213> ORGANISM: Artificial Sequence
<220> FEATURE:
<223> OTHER INFORMATION: synthetic

<400> SEQUENCE: 132

Phe Thr Thr Phe Thr Val Thr Lys Tyr
1               5

<210> SEQ ID NO 133
<211> LENGTH: 6
<212> TYPE: PRT
<213> ORGANISM: Artificial Sequence
<220> FEATURE:
<223> OTHER INFORMATION: synthetic

<400> SEQUENCE: 133

Phe Thr Val Thr Lys Tyr
1               5

<210> SEQ ID NO 134
<211> LENGTH: 4
<212> TYPE: PRT
<213> ORGANISM: Artificial Sequence
<220> FEATURE:
<223> OTHER INFORMATION: synthetic

<400> SEQUENCE: 134

Ala Ser Phe Thr
1

<210> SEQ ID NO 135
<211> LENGTH: 13
<212> TYPE: PRT
<213> ORGANISM: Artificial Sequence
<220> FEATURE:
<223> OTHER INFORMATION: synthetic

<400> SEQUENCE: 135

Trp Lys Ala Ser Phe Thr Thr Phe Thr Val Thr Lys Tyr
1               5                   10

<210> SEQ ID NO 136
<211> LENGTH: 9
<212> TYPE: PRT
<213> ORGANISM: Artificial Sequence
<220> FEATURE:
<223> OTHER INFORMATION: synthetic

<400> SEQUENCE: 136

Ser Phe Thr Thr Phe Thr Val Thr Lys
1               5

<210> SEQ ID NO 137
<211> LENGTH: 6
<212> TYPE: PRT
<213> ORGANISM: Artificial Sequence
<220> FEATURE:
<223> OTHER INFORMATION: synthetic

<400> SEQUENCE: 137

Thr Phe Thr Val Thr Lys
1               5

<210> SEQ ID NO 138
<211> LENGTH: 4
<212> TYPE: PRT
<213> ORGANISM: Artificial Sequence
<220> FEATURE:
<223> OTHER INFORMATION: synthetic

<400> SEQUENCE: 138

Lys Ala Ser Phe
1

<210> SEQ ID NO 139
<211> LENGTH: 13
<212> TYPE: PRT
<213> ORGANISM: Artificial Sequence
<220> FEATURE:
<223> OTHER INFORMATION: synthetic

<400> SEQUENCE: 139

Ile Trp Lys Ala Ser Phe Thr Thr Phe Thr Val Thr Lys
1               5                   10

<210> SEQ ID NO 140
<211> LENGTH: 9
<212> TYPE: PRT
<213> ORGANISM: Artificial Sequence
<220> FEATURE:
<223> OTHER INFORMATION: synthetic

<400> SEQUENCE: 140

Ala Ser Phe Thr Thr Phe Thr Val Thr
1               5

<210> SEQ ID NO 141
<211> LENGTH: 6
<212> TYPE: PRT
<213> ORGANISM: Artificial Sequence
<220> FEATURE:
<223> OTHER INFORMATION: synthetic

<400> SEQUENCE: 141

Thr Thr Phe Thr Val Thr
1               5

<210> SEQ ID NO 142
<211> LENGTH: 4
<212> TYPE: PRT
<213> ORGANISM: Artificial Sequence
<220> FEATURE:
<223> OTHER INFORMATION: synthetic

<400> SEQUENCE: 142

Trp Lys Ala Ser
1

```
<210> SEQ ID NO 143
<211> LENGTH: 13
<212> TYPE: PRT
<213> ORGANISM: Artificial Sequence
<220> FEATURE:
<223> OTHER INFORMATION: synthetic

<400> SEQUENCE: 143

Gly Ile Trp Lys Ala Ser Phe Thr Thr Phe Thr Val Thr
1               5                   10

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Lys Ala Ser Phe Thr Thr Phe Thr Val
1               5

<210> SEQ ID NO 145
<211> LENGTH: 6
<212> TYPE: PRT
<213> ORGANISM: Artificial Sequence
<220> FEATURE:
<223> OTHER INFORMATION: synthetic

<400> SEQUENCE: 145

Phe Thr Thr Phe Thr Val
1               5

<210> SEQ ID NO 146
<211> LENGTH: 4
<212> TYPE: PRT
<213> ORGANISM: Artificial Sequence
<220> FEATURE:
<223> OTHER INFORMATION: synthetic

<400> SEQUENCE: 146

Ile Trp Lys Ala
1

<210> SEQ ID NO 147
<211> LENGTH: 13
<212> TYPE: PRT
<213> ORGANISM: Artificial Sequence
<220> FEATURE:
<223> OTHER INFORMATION: synthetic

<400> SEQUENCE: 147

Asp Gly Ile Trp Lys Ala Ser Phe Thr Thr Phe Thr Val
1               5                   10

<210> SEQ ID NO 148
<211> LENGTH: 9
<212> TYPE: PRT
<213> ORGANISM: Artificial Sequence
<220> FEATURE:
<223> OTHER INFORMATION: synthetic

<400> SEQUENCE: 148

Trp Lys Ala Ser Phe Thr Thr Phe Thr
1               5

<210> SEQ ID NO 149
<211> LENGTH: 6
```

```
<212> TYPE: PRT
<213> ORGANISM: Artificial Sequence
<220> FEATURE:
<223> OTHER INFORMATION: synthetic

<400> SEQUENCE: 149

Ser Phe Thr Thr Phe Thr
1               5

<210> SEQ ID NO 150
<211> LENGTH: 4
<212> TYPE: PRT
<213> ORGANISM: Artificial Sequence
<220> FEATURE:
<223> OTHER INFORMATION: synthetic

<400> SEQUENCE: 150

Gly Ile Trp Lys
1

<210> SEQ ID NO 151
<211> LENGTH: 12
<212> TYPE: PRT
<213> ORGANISM: Artificial Sequence
<220> FEATURE:
<223> OTHER INFORMATION: synthetic

<400> SEQUENCE: 151

Thr Thr Phe Thr Val Thr Lys Tyr Trp Phe Tyr Arg
1               5                   10

<210> SEQ ID NO 152
<211> LENGTH: 9
<212> TYPE: PRT
<213> ORGANISM: Artificial Sequence
<220> FEATURE:
<223> OTHER INFORMATION: synthetic

<400> SEQUENCE: 152

Ile Trp Lys Ala Ser Phe Thr Thr Phe
1               5

<210> SEQ ID NO 153
<211> LENGTH: 6
<212> TYPE: PRT
<213> ORGANISM: Artificial Sequence
<220> FEATURE:
<223> OTHER INFORMATION: synthetic

<400> SEQUENCE: 153

Ala Ser Phe Thr Thr Phe
1               5

<210> SEQ ID NO 154
<211> LENGTH: 4
<212> TYPE: PRT
<213> ORGANISM: Artificial Sequence
<220> FEATURE:
<223> OTHER INFORMATION: synthetic

<400> SEQUENCE: 154

Asp Gly Ile Trp
1

<210> SEQ ID NO 155
<211> LENGTH: 12
<212> TYPE: PRT
<213> ORGANISM: Artificial Sequence
```

```
<220> FEATURE:
<223> OTHER INFORMATION: synthetic

<400> SEQUENCE: 155

Phe Thr Thr Phe Thr Val Thr Lys Tyr Trp Phe Tyr
1               5                   10

<210> SEQ ID NO 156
<211> LENGTH: 9
<212> TYPE: PRT
<213> ORGANISM: Artificial Sequence
<220> FEATURE:
<223> OTHER INFORMATION: synthetic

<400> SEQUENCE: 156

Gly Ile Trp Lys Ala Ser Phe Thr Thr
1               5

<210> SEQ ID NO 157
<211> LENGTH: 6
<212> TYPE: PRT
<213> ORGANISM: Artificial Sequence
<220> FEATURE:
<223> OTHER INFORMATION: synthetic

<400> SEQUENCE: 157

Lys Ala Ser Phe Thr Thr
1               5

<210> SEQ ID NO 158
<211> LENGTH: 12
<212> TYPE: PRT
<213> ORGANISM: Artificial Sequence
<220> FEATURE:
<223> OTHER INFORMATION: synthetic

<400> SEQUENCE: 158

Ser Phe Thr Thr Phe Thr Val Thr Lys Tyr Trp Phe
1               5                   10

<210> SEQ ID NO 159
<211> LENGTH: 9
<212> TYPE: PRT
<213> ORGANISM: Artificial Sequence
<220> FEATURE:
<223> OTHER INFORMATION: synthetic

<400> SEQUENCE: 159

Asp Gly Ile Trp Lys Ala Ser Phe Thr
1               5

<210> SEQ ID NO 160
<211> LENGTH: 8
<212> TYPE: PRT
<213> ORGANISM: Artificial Sequence
<220> FEATURE:
<223> OTHER INFORMATION: synthetic

<400> SEQUENCE: 160

Phe Ser Met Phe Arg Tyr Ser Asn
1               5

<210> SEQ ID NO 161
<211> LENGTH: 5
<212> TYPE: PRT
<213> ORGANISM: Artificial Sequence
<220> FEATURE:
<223> OTHER INFORMATION: synthetic
```

```
<400> SEQUENCE: 161

Ser Asn Trp Leu Asp
1               5

<210> SEQ ID NO 162
<211> LENGTH: 12
<212> TYPE: PRT
<213> ORGANISM: Artificial Sequence
<220> FEATURE:
<223> OTHER INFORMATION: synthetic

<400> SEQUENCE: 162

Phe Ser Met Phe Arg Tyr Ser Asn Trp Leu Asp Lys
1               5                   10

<210> SEQ ID NO 163
<211> LENGTH: 8
<212> TYPE: PRT
<213> ORGANISM: Artificial Sequence
<220> FEATURE:
<223> OTHER INFORMATION: synthetic

<400> SEQUENCE: 163

Val Phe Ser Met Phe Arg Tyr Ser
1               5

<210> SEQ ID NO 164
<211> LENGTH: 5
<212> TYPE: PRT
<213> ORGANISM: Artificial Sequence
<220> FEATURE:
<223> OTHER INFORMATION: synthetic

<400> SEQUENCE: 164

Tyr Ser Asn Trp Leu
1               5

<210> SEQ ID NO 165
<211> LENGTH: 12
<212> TYPE: PRT
<213> ORGANISM: Artificial Sequence
<220> FEATURE:
<223> OTHER INFORMATION: synthetic

<400> SEQUENCE: 165

Val Phe Ser Met Phe Arg Tyr Ser Asn Trp Leu Asp
1               5                   10

<210> SEQ ID NO 166
<211> LENGTH: 7
<212> TYPE: PRT
<213> ORGANISM: Artificial Sequence
<220> FEATURE:
<223> OTHER INFORMATION: synthetic

<400> SEQUENCE: 166

Tyr Ser Asn Trp Leu Asp Lys
1               5

<210> SEQ ID NO 167
<211> LENGTH: 5
<212> TYPE: PRT
<213> ORGANISM: Artificial Sequence
<220> FEATURE:
<223> OTHER INFORMATION: synthetic

<400> SEQUENCE: 167
```

Arg Tyr Ser Asn Trp
1               5

<210> SEQ ID NO 168
<211> LENGTH: 11
<212> TYPE: PRT
<213> ORGANISM: Artificial Sequence
<220> FEATURE:
<223> OTHER INFORMATION: synthetic

<400> SEQUENCE: 168

Ser Met Phe Arg Tyr Ser Asn Trp Leu Asp Lys
1               5                   10

<210> SEQ ID NO 169
<211> LENGTH: 7
<212> TYPE: PRT
<213> ORGANISM: Artificial Sequence
<220> FEATURE:
<223> OTHER INFORMATION: synthetic

<400> SEQUENCE: 169

Arg Tyr Ser Asn Trp Leu Asp
1               5

<210> SEQ ID NO 170
<211> LENGTH: 5
<212> TYPE: PRT
<213> ORGANISM: Artificial Sequence
<220> FEATURE:
<223> OTHER INFORMATION: synthetic

<400> SEQUENCE: 170

Phe Arg Tyr Ser Asn
1               5

<210> SEQ ID NO 171
<211> LENGTH: 11
<212> TYPE: PRT
<213> ORGANISM: Artificial Sequence
<220> FEATURE:
<223> OTHER INFORMATION: synthetic

<400> SEQUENCE: 171

Phe Ser Met Phe Arg Tyr Ser Asn Trp Leu Asp
1               5                   10

<210> SEQ ID NO 172
<211> LENGTH: 7
<212> TYPE: PRT
<213> ORGANISM: Artificial Sequence
<220> FEATURE:
<223> OTHER INFORMATION: synthetic

<400> SEQUENCE: 172

Phe Arg Tyr Ser Asn Trp Leu
1               5

<210> SEQ ID NO 173
<211> LENGTH: 5
<212> TYPE: PRT
<213> ORGANISM: Artificial Sequence
<220> FEATURE:
<223> OTHER INFORMATION: synthetic

<400> SEQUENCE: 173

Met Phe Arg Tyr Ser

<210> SEQ ID NO 174
<211> LENGTH: 11
<212> TYPE: PRT
<213> ORGANISM: Artificial Sequence
<220> FEATURE:
<223> OTHER INFORMATION: synthetic

<400> SEQUENCE: 174

Val Phe Ser Met Phe Arg Tyr Ser Asn Trp Leu
1               5                   10

<210> SEQ ID NO 175
<211> LENGTH: 7
<212> TYPE: PRT
<213> ORGANISM: Artificial Sequence
<220> FEATURE:
<223> OTHER INFORMATION: synthetic

<400> SEQUENCE: 175

Met Phe Arg Tyr Ser Asn Trp
1               5

<210> SEQ ID NO 176
<211> LENGTH: 5
<212> TYPE: PRT
<213> ORGANISM: Artificial Sequence
<220> FEATURE:
<223> OTHER INFORMATION: synthetic

<400> SEQUENCE: 176

Ser Met Phe Arg Tyr
1               5

<210> SEQ ID NO 177
<211> LENGTH: 10
<212> TYPE: PRT
<213> ORGANISM: Artificial Sequence
<220> FEATURE:
<223> OTHER INFORMATION: synthetic

<400> SEQUENCE: 177

Met Phe Arg Tyr Ser Asn Trp Leu Asp Lys
1               5                   10

<210> SEQ ID NO 178
<211> LENGTH: 7
<212> TYPE: PRT
<213> ORGANISM: Artificial Sequence
<220> FEATURE:
<223> OTHER INFORMATION: synthetic

<400> SEQUENCE: 178

Ser Met Phe Arg Tyr Ser Asn
1               5

<210> SEQ ID NO 179
<211> LENGTH: 5
<212> TYPE: PRT
<213> ORGANISM: Artificial Sequence
<220> FEATURE:
<223> OTHER INFORMATION: synthetic

<400> SEQUENCE: 179

Phe Ser Met Phe Arg
1               5

<210> SEQ ID NO 180
<211> LENGTH: 10
<212> TYPE: PRT
<213> ORGANISM: Artificial Sequence
<220> FEATURE:
<223> OTHER INFORMATION: synthetic

<400> SEQUENCE: 180

Ser Met Phe Arg Tyr Ser Asn Trp Leu Asp
1               5                   10

<210> SEQ ID NO 181
<211> LENGTH: 7
<212> TYPE: PRT
<213> ORGANISM: Artificial Sequence
<220> FEATURE:
<223> OTHER INFORMATION: synthetic

<400> SEQUENCE: 181

Phe Ser Met Phe Arg Tyr Ser
1               5

<210> SEQ ID NO 182
<211> LENGTH: 5
<212> TYPE: PRT
<213> ORGANISM: Artificial Sequence
<220> FEATURE:
<223> OTHER INFORMATION: synthetic

<400> SEQUENCE: 182

Val Phe Ser Met Phe
1               5

<210> SEQ ID NO 183
<211> LENGTH: 10
<212> TYPE: PRT
<213> ORGANISM: Artificial Sequence
<220> FEATURE:
<223> OTHER INFORMATION: synthetic

<400> SEQUENCE: 183

Phe Ser Met Phe Arg Tyr Ser Asn Trp Leu
1               5                   10

<210> SEQ ID NO 184
<211> LENGTH: 7
<212> TYPE: PRT
<213> ORGANISM: Artificial Sequence
<220> FEATURE:
<223> OTHER INFORMATION: synthetic

<400> SEQUENCE: 184

Val Phe Ser Met Phe Arg Tyr
1               5

<210> SEQ ID NO 185
<211> LENGTH: 4
<212> TYPE: PRT
<213> ORGANISM: Artificial Sequence
<220> FEATURE:
<223> OTHER INFORMATION: synthetic

<400> SEQUENCE: 185

Trp Leu Asp Lys
1

<210> SEQ ID NO 186

```
<211> LENGTH: 10
<212> TYPE: PRT
<213> ORGANISM: Artificial Sequence
<220> FEATURE:
<223> OTHER INFORMATION: synthetic

<400> SEQUENCE: 186

Val Phe Ser Met Phe Arg Tyr Ser Asn Trp
1               5                   10

<210> SEQ ID NO 187
<211> LENGTH: 6
<212> TYPE: PRT
<213> ORGANISM: Artificial Sequence
<220> FEATURE:
<223> OTHER INFORMATION: synthetic

<400> SEQUENCE: 187

Ser Asn Trp Leu Asp Lys
1               5

<210> SEQ ID NO 188
<211> LENGTH: 4
<212> TYPE: PRT
<213> ORGANISM: Artificial Sequence
<220> FEATURE:
<223> OTHER INFORMATION: synthetic

<400> SEQUENCE: 188

Asn Trp Leu Asp
1

<210> SEQ ID NO 189
<211> LENGTH: 9
<212> TYPE: PRT
<213> ORGANISM: Artificial Sequence
<220> FEATURE:
<223> OTHER INFORMATION: synthetic

<400> SEQUENCE: 189

Phe Arg Tyr Ser Asn Trp Leu Asp Lys
1               5

<210> SEQ ID NO 190
<211> LENGTH: 6
<212> TYPE: PRT
<213> ORGANISM: Artificial Sequence
<220> FEATURE:
<223> OTHER INFORMATION: synthetic

<400> SEQUENCE: 190

Tyr Ser Asn Trp Leu Asp
1               5

<210> SEQ ID NO 191
<211> LENGTH: 4
<212> TYPE: PRT
<213> ORGANISM: Artificial Sequence
<220> FEATURE:
<223> OTHER INFORMATION: synthetic

<400> SEQUENCE: 191

Ser Asn Trp Leu
1

<210> SEQ ID NO 192
<211> LENGTH: 9
<212> TYPE: PRT
```

<213> ORGANISM: Artificial Sequence
<220> FEATURE:
<223> OTHER INFORMATION: synthetic

<400> SEQUENCE: 192

Met Phe Arg Tyr Ser Asn Trp Leu Asp
1               5

<210> SEQ ID NO 193
<211> LENGTH: 6
<212> TYPE: PRT
<213> ORGANISM: Artificial Sequence
<220> FEATURE:
<223> OTHER INFORMATION: synthetic

<400> SEQUENCE: 193

Arg Tyr Ser Asn Trp Leu
1               5

<210> SEQ ID NO 194
<211> LENGTH: 4
<212> TYPE: PRT
<213> ORGANISM: Artificial Sequence
<220> FEATURE:
<223> OTHER INFORMATION: synthetic

<400> SEQUENCE: 194

Tyr Ser Asn Trp
1

<210> SEQ ID NO 195
<211> LENGTH: 9
<212> TYPE: PRT
<213> ORGANISM: Artificial Sequence
<220> FEATURE:
<223> OTHER INFORMATION: synthetic

<400> SEQUENCE: 195

Ser Met Phe Arg Tyr Ser Asn Trp Leu
1               5

<210> SEQ ID NO 196
<211> LENGTH: 6
<212> TYPE: PRT
<213> ORGANISM: Artificial Sequence
<220> FEATURE:
<223> OTHER INFORMATION: synthetic

<400> SEQUENCE: 196

Phe Arg Tyr Ser Asn Trp
1               5

<210> SEQ ID NO 197
<211> LENGTH: 4
<212> TYPE: PRT
<213> ORGANISM: Artificial Sequence
<220> FEATURE:
<223> OTHER INFORMATION: synthetic

<400> SEQUENCE: 197

Arg Tyr Ser Asn
1

<210> SEQ ID NO 198
<211> LENGTH: 9
<212> TYPE: PRT
<213> ORGANISM: Artificial Sequence
<220> FEATURE:

<223> OTHER INFORMATION: synthetic

<400> SEQUENCE: 198

Phe Ser Met Phe Arg Tyr Ser Asn Trp
1               5

<210> SEQ ID NO 199
<211> LENGTH: 6
<212> TYPE: PRT
<213> ORGANISM: Artificial Sequence
<220> FEATURE:
<223> OTHER INFORMATION: synthetic

<400> SEQUENCE: 199

Met Phe Arg Tyr Ser Asn
1               5

<210> SEQ ID NO 200
<211> LENGTH: 4
<212> TYPE: PRT
<213> ORGANISM: Artificial Sequence
<220> FEATURE:
<223> OTHER INFORMATION: synthetic

<400> SEQUENCE: 200

Phe Arg Tyr Ser
1

<210> SEQ ID NO 201
<211> LENGTH: 9
<212> TYPE: PRT
<213> ORGANISM: Artificial Sequence
<220> FEATURE:
<223> OTHER INFORMATION: synthetic

<400> SEQUENCE: 201

Val Phe Ser Met Phe Arg Tyr Ser Asn
1               5

<210> SEQ ID NO 202
<211> LENGTH: 6
<212> TYPE: PRT
<213> ORGANISM: Artificial Sequence
<220> FEATURE:
<223> OTHER INFORMATION: synthetic

<400> SEQUENCE: 202

Ser Met Phe Arg Tyr Ser
1               5

<210> SEQ ID NO 203
<211> LENGTH: 4
<212> TYPE: PRT
<213> ORGANISM: Artificial Sequence
<220> FEATURE:
<223> OTHER INFORMATION: synthetic

<400> SEQUENCE: 203

Met Phe Arg Tyr
1

<210> SEQ ID NO 204
<211> LENGTH: 8
<212> TYPE: PRT
<213> ORGANISM: Artificial Sequence
<220> FEATURE:
<223> OTHER INFORMATION: synthetic

```
<400> SEQUENCE: 204

Arg Tyr Ser Asn Trp Leu Asp Lys
1               5

<210> SEQ ID NO 205
<211> LENGTH: 6
<212> TYPE: PRT
<213> ORGANISM: Artificial Sequence
<220> FEATURE:
<223> OTHER INFORMATION: synthetic

<400> SEQUENCE: 205

Phe Ser Met Phe Arg Tyr
1               5

<210> SEQ ID NO 206
<211> LENGTH: 4
<212> TYPE: PRT
<213> ORGANISM: Artificial Sequence
<220> FEATURE:
<223> OTHER INFORMATION: synthetic

<400> SEQUENCE: 206

Ser Met Phe Arg
1

<210> SEQ ID NO 207
<211> LENGTH: 8
<212> TYPE: PRT
<213> ORGANISM: Artificial Sequence
<220> FEATURE:
<223> OTHER INFORMATION: synthetic

<400> SEQUENCE: 207

Phe Arg Tyr Ser Asn Trp Leu Asp
1               5

<210> SEQ ID NO 208
<211> LENGTH: 6
<212> TYPE: PRT
<213> ORGANISM: Artificial Sequence
<220> FEATURE:
<223> OTHER INFORMATION: synthetic

<400> SEQUENCE: 208

Val Phe Ser Met Phe Arg
1               5

<210> SEQ ID NO 209
<211> LENGTH: 4
<212> TYPE: PRT
<213> ORGANISM: Artificial Sequence
<220> FEATURE:
<223> OTHER INFORMATION: synthetic

<400> SEQUENCE: 209

Phe Ser Met Phe
1

<210> SEQ ID NO 210
<211> LENGTH: 8
<212> TYPE: PRT
<213> ORGANISM: Artificial Sequence
<220> FEATURE:
<223> OTHER INFORMATION: synthetic

<400> SEQUENCE: 210
```

```
Met Phe Arg Tyr Ser Asn Trp Leu
1               5
```

<210> SEQ ID NO 211
<211> LENGTH: 5
<212> TYPE: PRT
<213> ORGANISM: Artificial Sequence
<220> FEATURE:
<223> OTHER INFORMATION: synthetic

<400> SEQUENCE: 211

```
Asn Trp Leu Asp Lys
1               5
```

<210> SEQ ID NO 212
<211> LENGTH: 4
<212> TYPE: PRT
<213> ORGANISM: Artificial Sequence
<220> FEATURE:
<223> OTHER INFORMATION: synthetic

<400> SEQUENCE: 212

```
Val Phe Ser Met
1
```

<210> SEQ ID NO 213
<211> LENGTH: 8
<212> TYPE: PRT
<213> ORGANISM: Artificial Sequence
<220> FEATURE:
<223> OTHER INFORMATION: synthetic

<400> SEQUENCE: 213

```
Ser Met Phe Arg Tyr Ser Asn Trp
1               5
```

<210> SEQ ID NO 214
<211> LENGTH: 1280
<212> TYPE: PRT
<213> ORGANISM: Homo sapiens

<400> SEQUENCE: 214

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160
```

```
Gly Trp Phe Asp Val His Asp Val Gly Glu Leu Asn Thr Arg Leu Thr
                165                 170                 175

Asp Asp Val Ser Lys Ile Asn Glu Gly Ile Asp Lys Ile Gly Met
            180                 185                 190

Phe Phe Gln Ser Met Ala Thr Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590
```

```
Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
        610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
        690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
        770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
        850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ser Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
        930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys  Ala Lys Ile Ser Ala  Ala His Ile
        995                 1000                 1005

Ile Met  Ile Ile Glu Lys Thr  Pro Leu Ile Asp Ser  Tyr Ser Thr
```

-continued

```
              1010                1015                1020
Glu Gly Leu Met Pro Asn Thr Leu Glu Gly Asn Val Thr Phe Gly
            1025                1030                1035
Glu Val Val Phe Asn Tyr Pro Thr Arg Pro Asp Ile Pro Val Leu
            1040                1045                1050
Gln Gly Leu Ser Leu Glu Val Lys Lys Gly Gln Thr Leu Ala Leu
            1055                1060                1065
Val Gly Ser Ser Gly Cys Gly Lys Ser Thr Val Val Gln Leu Leu
            1070                1075                1080
Glu Arg Phe Tyr Asp Pro Leu Ala Gly Lys Val Leu Leu Asp Gly
            1085                1090                1095
Lys Glu Ile Lys Arg Leu Asn Val Gln Trp Leu Arg Ala His Leu
            1100                1105                1110
Gly Ile Val Ser Gln Glu Pro Ile Leu Phe Asp Cys Ser Ile Ala
            1115                1120                1125
Glu Asn Ile Ala Tyr Gly Asp Asn Ser Arg Val Val Ser Gln Glu
            1130                1135                1140
Glu Ile Val Arg Ala Ala Lys Glu Ala Asn Ile His Ala Phe Ile
            1145                1150                1155
Glu Ser Leu Pro Asn Lys Tyr Ser Thr Lys Val Gly Asp Lys Gly
            1160                1165                1170
Thr Gln Leu Ser Gly Gly Gln Lys Gln Arg Ile Ala Ile Ala Arg
            1175                1180                1185
Ala Leu Val Arg Gln Pro His Ile Leu Leu Leu Asp Glu Ala Thr
            1190                1195                1200
Ser Ala Leu Asp Thr Glu Ser Glu Lys Val Val Gln Glu Ala Leu
            1205                1210                1215
Asp Lys Ala Arg Glu Gly Arg Thr Cys Ile Val Ile Ala His Arg
            1220                1225                1230
Leu Ser Thr Ile Gln Asn Ala Asp Leu Ile Val Val Phe Gln Asn
            1235                1240                1245
Gly Arg Val Lys Glu His Gly Thr His Gln Gln Leu Leu Ala Gln
            1250                1255                1260
Lys Gly Ile Tyr Phe Ser Met Val Ser Val Gln Ala Gly Thr Lys
            1265                1270                1275
Arg Gln
    1280

<210> SEQ ID NO 215
<211> LENGTH: 178
<212> TYPE: PRT
<213> ORGANISM: Homo sapiens

<400> SEQUENCE: 215

Met Ser Gly Gly Lys Tyr Val Asp Ser Glu Gly His Leu Tyr Thr Val
1               5                   10                  15
Pro Ile Arg Glu Gln Gly Asn Ile Tyr Lys Pro Asn Asn Lys Ala Met
            20                  25                  30
Ala Asp Glu Leu Ser Glu Lys Gln Val Tyr Asp Ala His Thr Lys Glu
        35                  40                  45
Ile Asp Leu Val Asn Arg Asp Pro Lys His Leu Asn Asp Asp Val Val
    50                  55                  60
Lys Ile Asp Phe Glu Asp Val Ile Ala Glu Pro Glu Gly Thr His Ser
65                  70                  75                  80
Phe Asp Gly Ile Trp Lys Ala Ser Phe Thr Thr Phe Thr Val Thr Lys
```

-continued

```
                      85                      90                      95
Tyr Trp Phe Tyr Arg Leu Leu Ser Ala Leu Phe Gly Ile Pro Met Ala
                100                     105                     110

Leu Ile Trp Gly Ile Tyr Phe Ala Ile Leu Ser Phe Leu His Ile Trp
            115                     120                     125

Ala Val Val Pro Cys Ile Lys Ser Phe Leu Ile Glu Ile Gln Cys Ile
        130                     135                     140

Ser Arg Val Tyr Ser Ile Tyr Val His Thr Val Cys Asp Pro Leu Phe
145                     150                     155                 160

Glu Ala Val Gly Lys Ile Phe Ser Asn Val Arg Ile Asn Leu Gln Lys
                165                     170                     175

Glu Ile
```